US010101274B2

(12) United States Patent
Lemieux et al.

(10) Patent No.: US 10,101,274 B2
(45) Date of Patent: Oct. 16, 2018

(54) OPTICAL INTERROGATION DEVICE

(71) Applicants: GenePOC inc., Québec (CA); UNIVERSITÉ LAVAL, Québec (CA)

(72) Inventors: Hugo Lemieux, Lévis (CA); Sébastien Chapdelaine, Lévis (CA); David Béliveau-Viel, Québec (CA); Jean-François Gravel, Stoneham-et-Tewkesbury (CA)

(73) Assignees: GenePOC INC., Québec, QC (CA); Universite Laval, Québec, QC (CA)

( * ) Notice: Subject to any disclaimer, the term of this patent is extended or adjusted under 35 U.S.C. 154(b) by 192 days.

(21) Appl. No.: 14/649,660

(22) PCT Filed: Dec. 5, 2013

(86) PCT No.: PCT/IB2013/060686
§ 371 (c)(1),
(2) Date: Jun. 4, 2015

(87) PCT Pub. No.: WO2014/087380
PCT Pub. Date: Jun. 12, 2014

(65) Prior Publication Data
US 2015/0308958 A1    Oct. 29, 2015

Related U.S. Application Data

(60) Provisional application No. 61/733,653, filed on Dec. 5, 2012, provisional application No. 61/813,864, filed on Apr. 19, 2013.

(51) Int. Cl.
*G01N 3/00* (2006.01)
*G01N 21/00* (2006.01)
(Continued)

(52) U.S. Cl.
CPC .......... *G01N 21/6486* (2013.01); *G01J 3/443* (2013.01); *G01N 21/645* (2013.01);
(Continued)

(58) Field of Classification Search
CPC ..... B01L 2300/0627; B01L 2300/0654; G01N 2021/6419; G01N 2021/6471; G01N 2021/6484; G01N 21/6486
See application file for complete search history.

(56) References Cited

U.S. PATENT DOCUMENTS

| 4,343,991 A | 8/1982 | Fujiwara et al. |
| 5,162,654 A | 11/1992 | Kostichka et al. |

(Continued)

FOREIGN PATENT DOCUMENTS

| CN | 1808204 A | 7/2006 |
| CN | 101251486 A | 8/2008 |

(Continued)

OTHER PUBLICATIONS

Anderson et al., "Multi-analyte interrogation using the fiber optic biosensor", Biosensors & Bioelectronics, 2000, pp. 771-777, vol. 14, Elsevier, United States.

(Continued)

*Primary Examiner* — Nathan A Bowers
(74) *Attorney, Agent, or Firm* — Fasken Martineau Dumoulin

(57) ABSTRACT

An interrogation device for detecting luminescent light produced by analytes in a sample excited by multiple excitation light beams each having individual spectral contents, comprising a plurality of light sources each generating an excitation light beam; at least one detector for detecting the luminescent light produced by the sample; and an optical assembly defining distinct and fixed excitation light paths for each of the excitation light beams from the light sources (Continued)

to a common excitation site on the sample and defining a shared luminescence light path for the luminescent light from the excitation site on sample to the at least one detector, the excitation light paths and the luminescence light path being on a same side of the sample, the optical assembly including sample-side optics projecting the excitation light towards the sample and collecting luminescent light from the sample.

11 Claims, 32 Drawing Sheets

(51) Int. Cl.
    *G01N 21/64* (2006.01)
    *G01J 3/443* (2006.01)
    *G01N 21/76* (2006.01)
    *G01J 3/02* (2006.01)
    *G01J 3/10* (2006.01)

(52) U.S. Cl.
    CPC ..... *G01N 21/6408* (2013.01); *G01N 21/6445* (2013.01); *G01N 21/763* (2013.01); *G01J 3/021* (2013.01); *G01J 3/0213* (2013.01); *G01J 3/0216* (2013.01); *G01J 3/0218* (2013.01); *G01J 2003/102* (2013.01); *G01N 2021/6419* (2013.01); *G01N 2021/6471* (2013.01); *G01N 2021/6484* (2013.01); *G01N 2201/061* (2013.01)

(56) References Cited

U.S. PATENT DOCUMENTS

| | | |
|---|---|---|
| 5,272,090 A | 12/1993 | Gavish et al. |
| 5,675,155 A | 10/1997 | Pentoney, Jr. et al. |
| 5,813,987 A | 9/1998 | Modell et al. |
| 6,096,272 A * | 8/2000 | Clark ............... G01N 21/253 422/64 |
| 6,352,672 B1 * | 3/2002 | Mabile ............... G01N 21/6428 250/458.1 |
| 6,388,788 B1 * | 5/2002 | Harris ............... G02B 21/0028 250/234 |
| 6,819,411 B1 * | 11/2004 | Sharpe ............... G01N 15/1436 250/461.2 |
| 6,828,567 B2 | 12/2004 | Amirkhanian et al. |
| 6,930,314 B2 | 8/2005 | Jackson, III et al. |
| 6,940,598 B2 | 9/2005 | Christel et al. |
| 7,709,249 B2 | 5/2010 | Bedingham et al. |
| 7,879,598 B2 | 2/2011 | Zesch et al. |
| 8,137,616 B2 | 3/2012 | Sagner et al. |
| 2002/0109844 A1 | 8/2002 | Christel et al. |
| 2005/0151094 A1 | 7/2005 | Kitagawa |
| 2005/0286047 A1 | 12/2005 | Boege |
| 2006/0252079 A1 * | 11/2006 | Oldham ............... B82Y 5/00 435/6.13 |
| 2007/0194247 A1 | 8/2007 | Reid et al. |
| 2008/0179541 A1 | 7/2008 | Leboeuf et al. |
| 2009/0024331 A1 | 1/2009 | Tomaney et al. |
| 2009/0152474 A1 | 6/2009 | Berger et al. |
| 2009/0309049 A1 | 12/2009 | Van Dijk et al. |
| 2010/0096561 A1 | 4/2010 | Johnson et al. |
| 2011/0160073 A1 | 6/2011 | Kordunsky et al. |
| 2011/0210257 A9 | 9/2011 | Handique et al. |
| 2012/0087832 A1 * | 4/2012 | King ............... G01N 21/6428 422/82.08 |
| 2013/0010288 A1 | 1/2013 | Dwyer et al. |

FOREIGN PATENT DOCUMENTS

| | | |
|---|---|---|
| CN | 101287980 A | 10/2008 |
| CN | 201785391 U | 4/2011 |
| CN | 102341710 A | 2/2012 |
| EP | 1681555 A1 | 7/2006 |
| JP | 2001509266 A | 7/2001 |
| JP | 2005526253 A | 9/2005 |
| JP | 2008039605 A | 2/2008 |
| JP | 2010043983 A | 2/2010 |
| WO | 9834094 A1 | 8/1998 |
| WO | 9908096 A1 | 2/1999 |
| WO | 03098278 A2 | 11/2003 |
| WO | 2006102297 A1 | 9/2006 |
| WO | 2010079338 A2 | 7/2010 |
| WO | 2011110338 A1 | 9/2011 |
| WO | 2012120463 A1 | 9/2012 |
| WO | 2013014540 A2 | 1/2013 |
| WO | 2013092766 A1 | 6/2013 |

OTHER PUBLICATIONS

Pravinata et al., "Eryhrosin B Phosphorescence Monitors Molecular Mobility and Dynamic Site Heterogeneity in Amorphous Sucrose", Biophysical Journal, May 2005, pp. 3551-3561, vol. 88, Biophysical Society, United States.

* cited by examiner

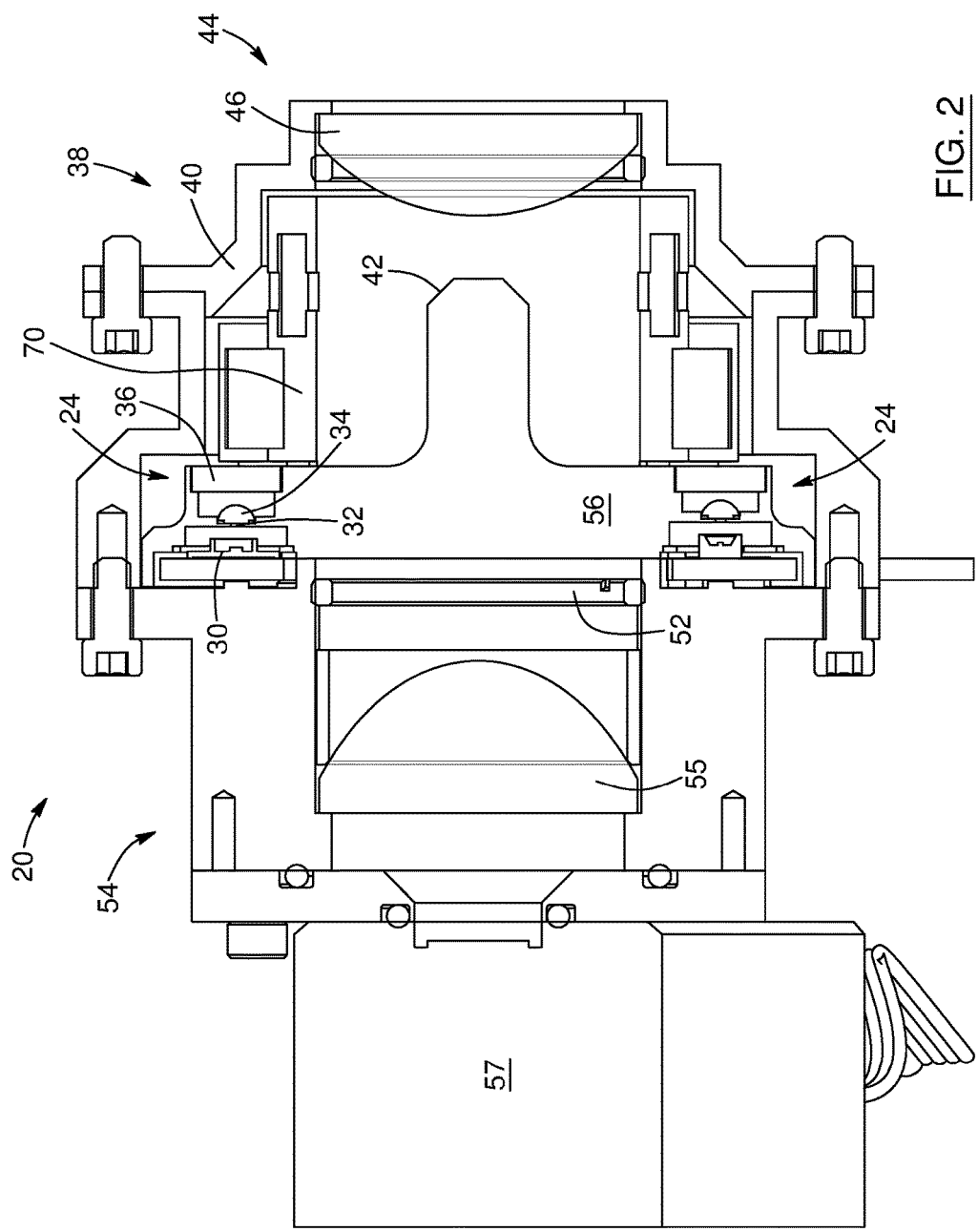

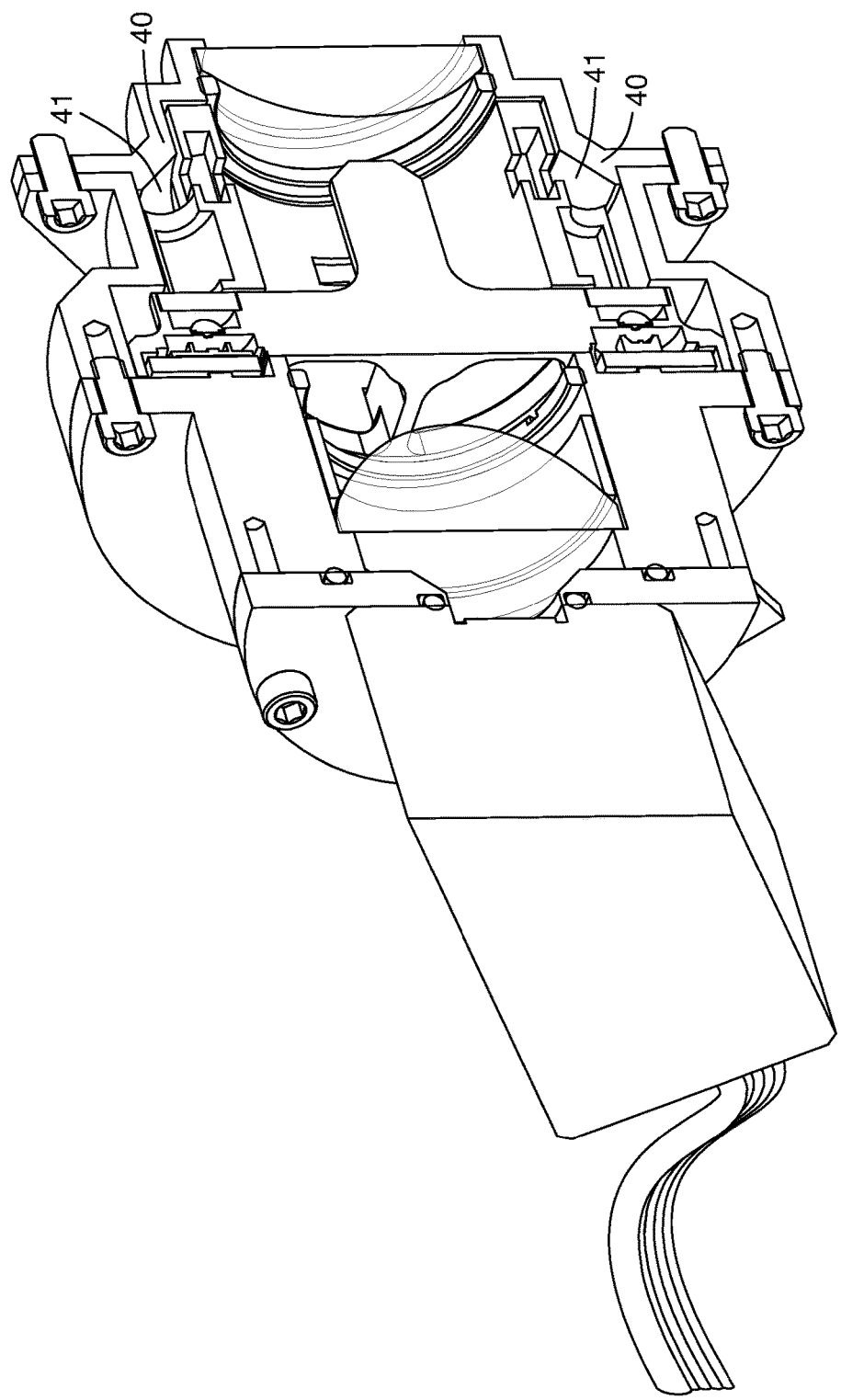

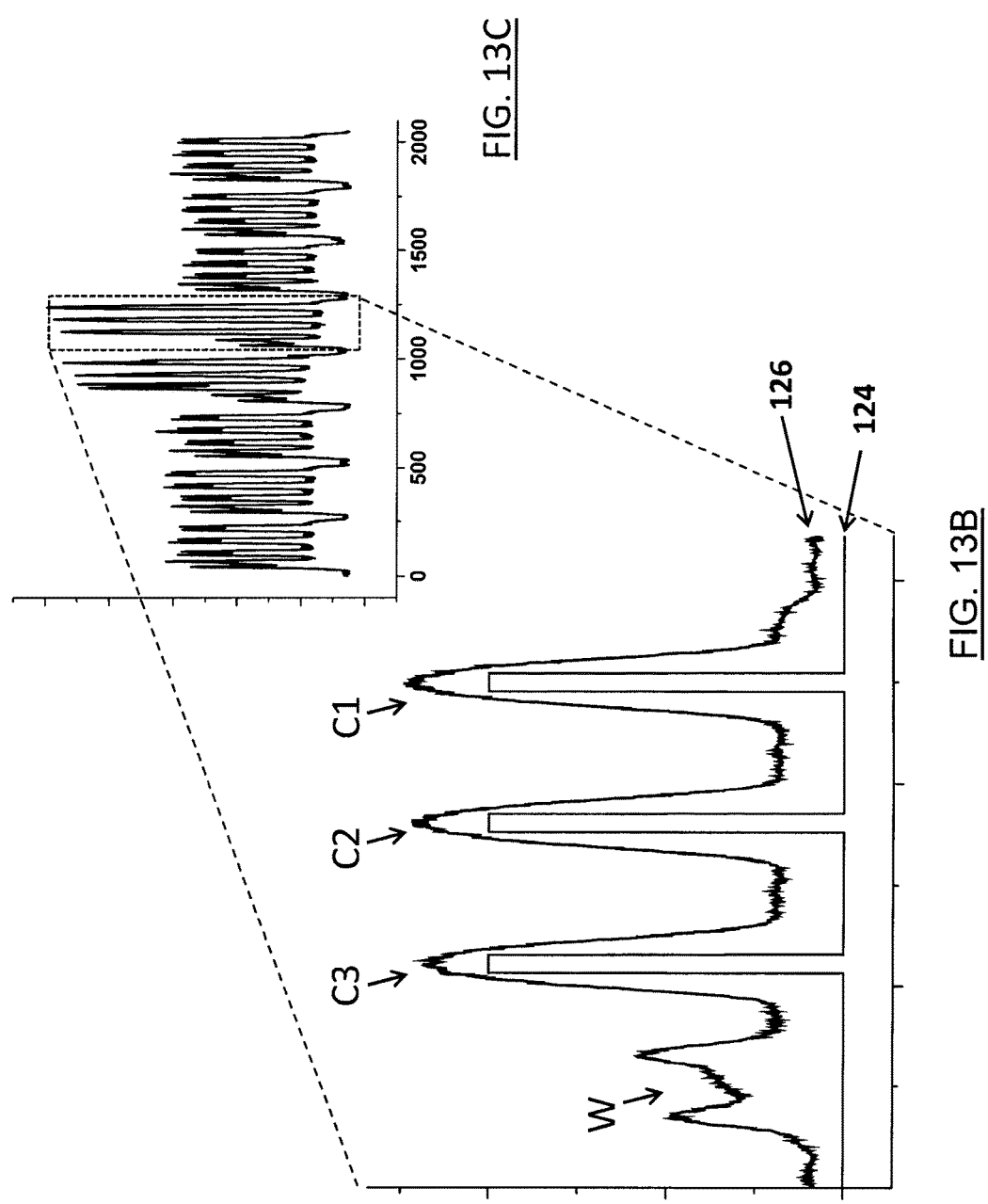

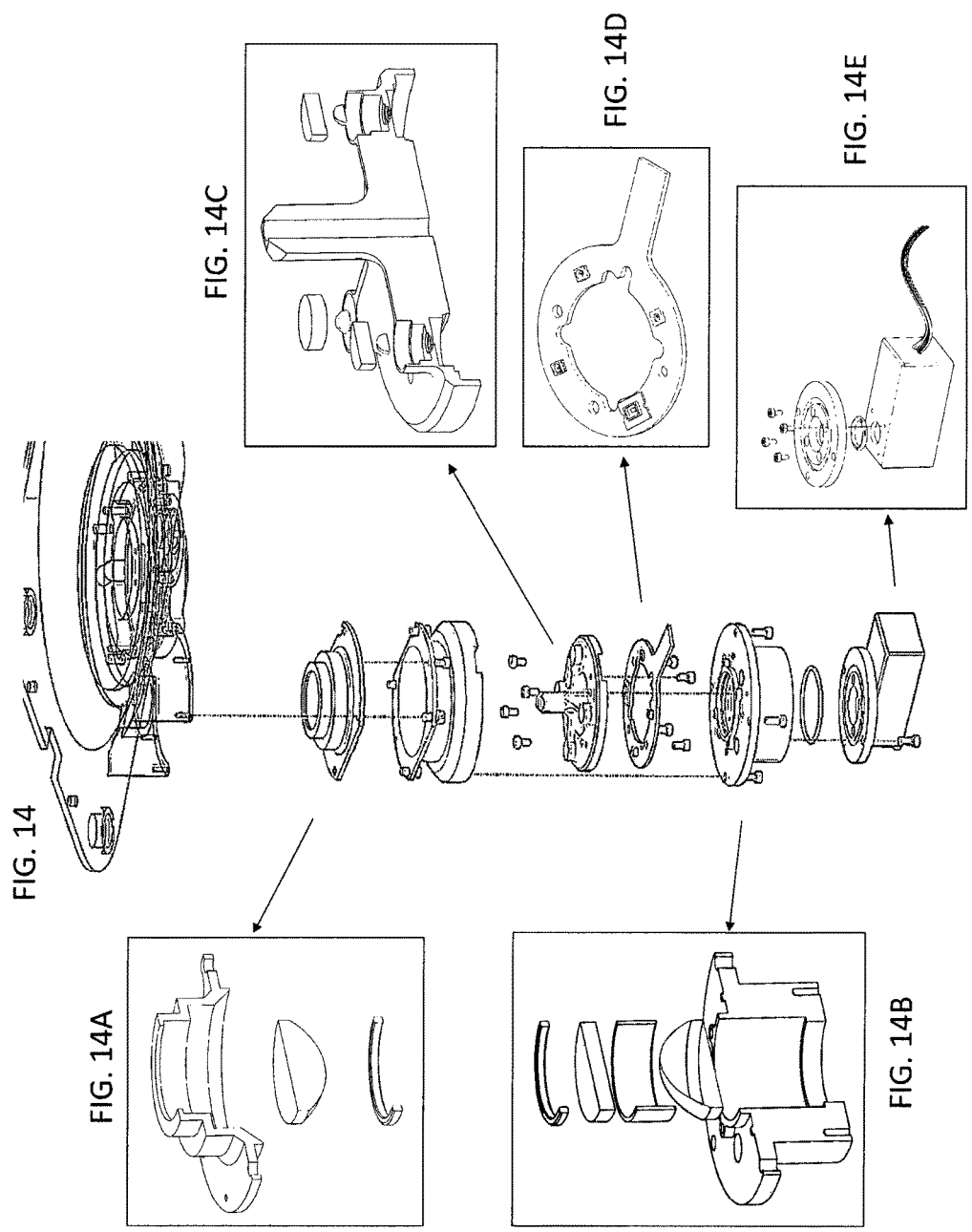

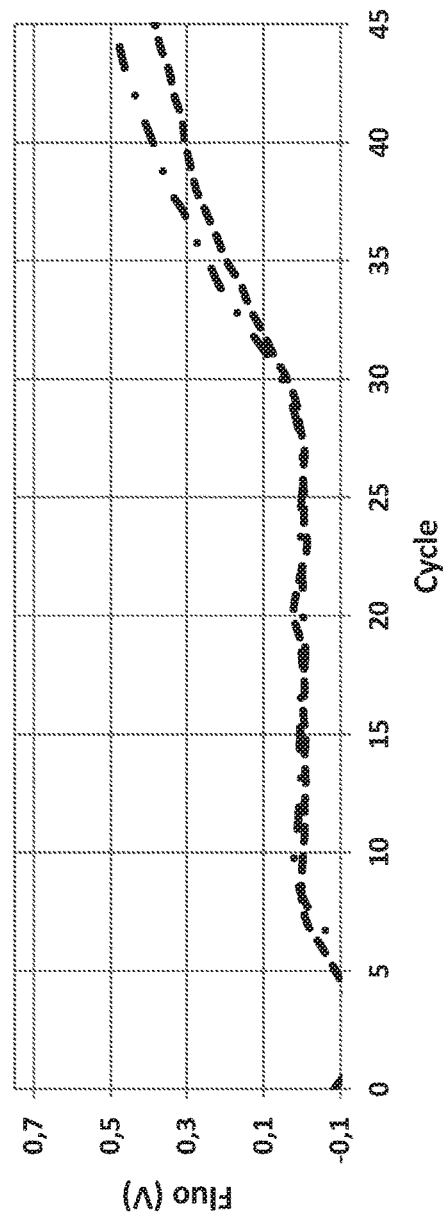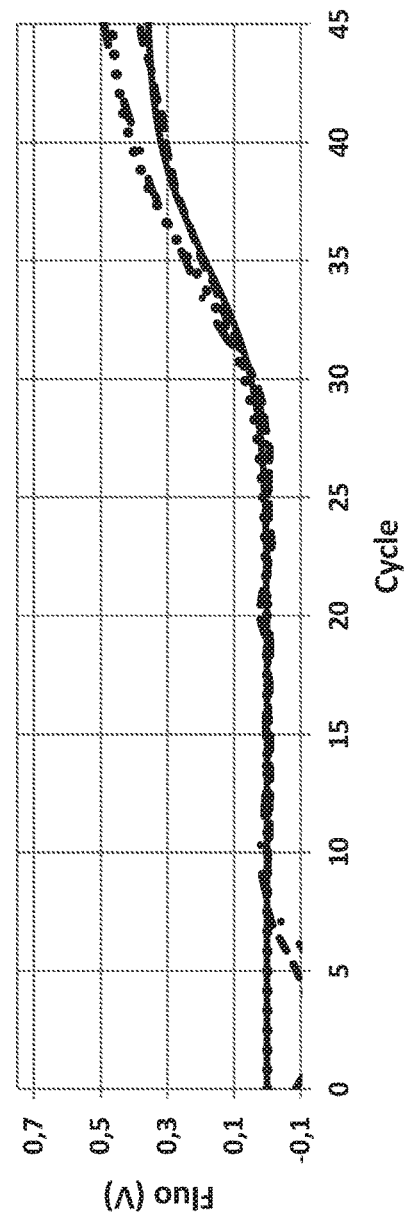
FIGURE 19A
FIGURE 19B
• • • • GBS Target ——— Internal Control

OPTICAL INTERROGATION DEVICE

TECHNICAL FIELD

The present invention relates to optical interrogation techniques, and more particularly concerns a device for interrogating different fluorophores or the like in a sample.

BACKGROUND OF THE ART

Fluorophores are compounds which generate light as a result of optical excitation. They are used in several fields, such as diagnostic assays. For example, medical diagnostic systems use optical interrogation of fluorophores in assay solutions to measure nucleic acids amplification inside containers such as microfluidic cartridges.

Typically, fluorescent-based processes involve directing excitation light on a specific fluorophore element, which is known to absorb light within a specific excitation wavelength band and emit, as a result, fluorescent light within a different wavelength range. The emitted light is collected and filtered so that only the fluorescence remains and is detected.

For some applications, it is advantageous to use light within different wavelength bands to excite a same assay or sample. This is for example the case when a sample is tested using multiple fluorophores, each having a specific excitation spectral profile. Applications studying other optical phenomena where a sample is excited by light at one wavelength and emits light at another wavelength are also known in the art.

In some cases, it may be desirable for the optical device to be able to switch between different wavelengths rapidly. For example, it is the case with real-time polymerase chain reaction (rtPCR) systems where different samples are mounted circumferentially on a rotating holder for optical analysis. As the holder rotates, fluorescence measurements are performed for each thermal cycle. In order to perform such acquisitions at different wavelengths the interrogation system needs to switch between excitation light sources quickly enough to limit down time between acquisitions, which impacts on the total time of the PCR procedure. Traditional systems using mechanical switching between different light sources or fluorescence filters (such as filter wheels) often introduce substantial delays in the acquisition process. Other systems use different optical interrogation devices altogether for different wavelengths, which can greatly increase the overall cost and complexity of the system.

There is therefore a need for an improved optical excitation and interrogation device allowing the use of different excitation and detection wavelengths and a rapid detection of multiple fluorophores in a sample.

SUMMARY

Embodiments of the present invention provide an optical interrogation device for detecting luminescent light from analytes in a sample using excitation light at a plurality of wavelengths. The device includes multiple light source assemblies each emitting excitation light with individual spectral contents. The excitation light is projected on the sample to excite the analytes. The resulting luminescent light travels back through the device and is filtered to isolate the spectral content of interest from parasitic light (such as excitation light) before being outputted for detection.

In one embodiment, the optical interrogation device can be used to detect luminesence from molecular species referred to as fluorophores. Embodiments of the invention can be used to detect luminescent light from analytes in a sample resulting from various optical phenomena such as phosphorescence, fluorescence, bioluminescence, time-resolved luminescence, polarization fluorescence, etc. For example, fluorescence detection can be used in real-time PCR, nucleic acid sequencing, protein analysis, cell analysis, etc.

In accordance with one aspect, there is provided an interrogation device for detecting luminescent light produced by a sample excited by multiple excitation light beams having individual spectral contents, comprising: a plurality of light source assemblies each generating one of the excitation light beams; at least one detector for detecting the luminescent light produced by the sample; and an optical assembly defining different excitation light paths for each of the excitation light beams from the light source assembly to a common excitation site on the sample and defining a luminescence light path for the luminescent light from the excitation site on sample to the at least one detector.

The optical assembly is contained in a single housing.

The optical assembly may include components to shape the spatial and/or the spectral profile of both the excitation and luminescent light and to prevent parasitic light from reaching the detector. For example, spatial filters limiting the size of a given light beam along the corresponding light path may be provided at several locations within the assembly. A spectral filter having a spectral profile excluding the spectral contents of the excitation beams may also be disposed in the luminescence light path.

The optical assembly may include sample-side optics projecting the excitation light towards the sample and collecting fluorescent light from the sample. Detector-side optics outputting the filtered fluorescent light for detection may be provided as well.

In an exemplary embodiment, the optical components of the optical assembly are attached rigidly within the housing and define the different light paths throughout the device having taken into account geometrical considerations. For example, in one embodiment the light sources are peripherally distributed about a main axis and a mirror assembly including an outer reflective element is disposed in the path of the excitation beams from the light sources to inwardly redirect the same. An inner reflective element receiving the excitation light beams from the outer reflecting element and redirecting the same in the forward direction may be further provided. However, it will be further understood that other configurations may be devised without departing from the scope of the invention.

In accordance with another aspect of the invention, there is also provided a test apparatus for optically testing a sample, including an optical interrogation device as described above. The test apparatus may for example be embodied by systems for, non-limitatively, Polymerase Chain Reaction (PCR), real-time Polymerase Chain Reaction (rtPCR), isothermal amplification such as Recombination Polymerase Amplification (RPA) or other nucleic acid detection methods.

In accordance with still another aspect of the invention, there is provided an interrogation device for detecting luminescent light produced by analytes in a sample excited by multiple excitation light beams each having individual spectral contents. The interrogation device comprises a plurality of light sources each generating one of the multiple excitation light beams, the excitation light beams being projected on the sample to excite the analytes; at least one detector for detecting the luminescent light produced by the sample; and an optical assembly defining distinct and fixed excitation light paths for each of the excitation light beams from the light sources to a common excitation site on the sample and defining a shared luminescence light path for the luminescent light from the excitation site on sample to the at least one detector, the excitation light paths and the luminescence light path being on a same side of the sample, the optical assembly including sample-side optics projecting the excitation light towards the sample and collecting luminescent light from the sample, the optical assembly providing the sample-side optics in all of the excitation light paths and in the shared luminescence light path.

In one embodiment, the optical assembly further comprises a filter provided in the shared luminescence light path, wherein the filter is one of a fixed filter and an actuated filter and wherein the filter is one of a single-band-pass filter and a multi-band-pass filter.

In one embodiment, the optical assembly is contained in a single housing.

In one embodiment, the optical assembly includes a component to shape at least one of a spatial and a spectral profile of at least one of the excitation light beam and the luminescent light.

In one embodiment, the component is a spatial filter limiting a size of a given light beam along a corresponding light path.

In one embodiment, the spectral filter has a spectral profile excluding the spectral contents of the excitation beam and is disposed in the luminescence light path.

In one embodiment, the optical assembly includes detector-side optics outputting the filtered luminescent light for detection.

In one embodiment, the light sources are peripherally distributed about a main axis and wherein the optical assembly includes a mirror assembly including an outer reflective element disposed in the path of the excitation beams from the light sources to inwardly redirect the excitation beams.

In one embodiment, the mirror assembly includes an inner reflective element to receive the excitation light beams from the outer reflecting element and redirect the excitation light beams toward the sample-side optics.

In one embodiment, the optical assembly comprises waveguides to guide the excitation light beams towards the sample-side optics.

In one embodiment, the luminescent light from analytes in the sample result from at least one optical phenomena, the optical phenomena being one of fluorescence, phosphorescence, bioluminescence, time-resolved luminescence and polarization fluorescence.

In accordance with still another aspect of the invention, there is provided a test apparatus for optically testing a sample, including an optical interrogation device.

In one embodiment, the test apparatus is embodied by a system for performing one of Polymerase Chain Reaction (PCR), real-time Polymerase Chain Reaction (rtPCR), isothermal amplification Recombination Polymerase Amplification (RPA) and other nucleic acid detection methods.

Further examples including an optical interrogation device as described above include nucleic acid sequencing, protein analysis, cell analysis and any other system requiring the excitation and detection using multiple wavelengths.

Other features and advantages of embodiments of the invention will be better understood upon reading of embodiments thereof with reference to the appended drawings.

BRIEF DESCRIPTION OF THE DRAWINGS

Having thus generally described the nature of the invention, reference will now be made to the accompanying drawings, showing by way of illustration a preferred embodiment thereof and in which:

FIG. 2 is a cross-sectional side view of an example optical assembly defining a fluorescence device;

FIG. 3 is a cross-sectional isometric view of the device of FIG. 2;

FIG. 13B shows signal traces acquired using a test apparatus such as shown in FIG. 12 and FIG. 13C shows the raw signal acquired for a complete rotation of 8 fluidic centripetal devices of the type shown in FIG. 13A;

FIG. 14 shows exploded views of example optical module components and assembly including FIG. 14A—Distal Tube, FIG. 14B—PMT Tube, FIG. 14C—LED Optics, FIG. 14D—LED Printed Circuit Board and FIG. 14E—Detector module;

FIGS. 19A and 19B show the Raw data (bkg sub) and fitted curves for well 2 in the example experiment of FIG. 18.

It will be noted that throughout the appended drawings, like features are identified by like reference numerals.

DETAILED DESCRIPTION

Exemplary embodiments of the present invention relate to optical interrogation devices.

An interrogation device for detecting luminescent light produced by analytes in a sample excited by multiple excitation light beams each having individual spectral contents is provided. The interrogation device comprises a plurality of light sources each generating an excitation light beam; at least one detector for detecting the luminescent light produced by the sample; and an optical assembly defining distinct and fixed excitation light paths for each of the excitation light beams from the light sources to a common excitation site on the sample and defining a shared luminescence light path for the luminescent light from the excitation site on sample to the at least one detector, the excitation light paths and the luminescence light path being on a same side of the sample, the optical assembly including sample-side optics projecting the excitation light towards the sample and collecting luminescent light from the sample.

Figure 12:
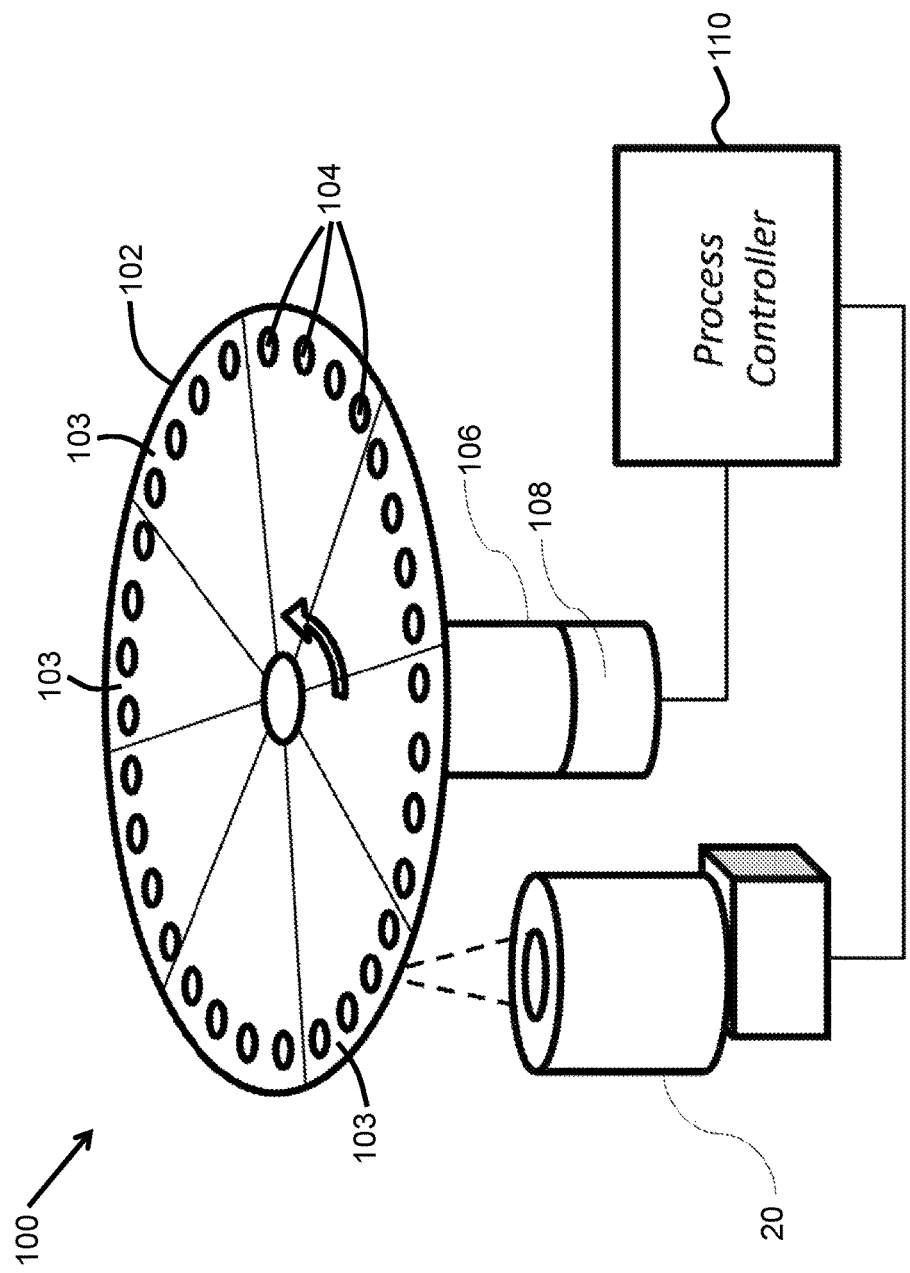
FIG. 12 is a schematic representation of a test apparatus in which an example optical interrogation devices may be used, for example as part of a PCR system.

In one exemplary embodiment, optical interrogation devices 20 may be useful in a test apparatus 100 such as the one schematically shown in FIG. 12. Such test apparatuses 100 include a rotor 102 on which a plurality of fluidic centripetal devices 103 are disposed radially. The samples for analysis are loaded on the fluidic centripetal devices 103 and are contained into microfluidic containers 104. Examples of fluidic centripetal devices suitable for real-time PCR acquisition techniques and the like are shown in PCT Pat. Appl. Publ. No. WO 2012/120463 which is hereby incorporated by reference. The rotational movement of the rotor 102 is produced by an actuator 106 receiving control signals from a process controller 110. An encoder 108 provides position signals feedback to the controller for precise feedback-loop control. The actuator 106 and optical interrogation device 20 are jointly controlled by the process controller 110 which activates the interrogation device according to a desired acquisition routine. Data acquisition and signal processing are performed in proper synchronization with the rotation of the rotor 102 using the encoder signal, the latter defining data acquisition "windows".

Figure 13A:
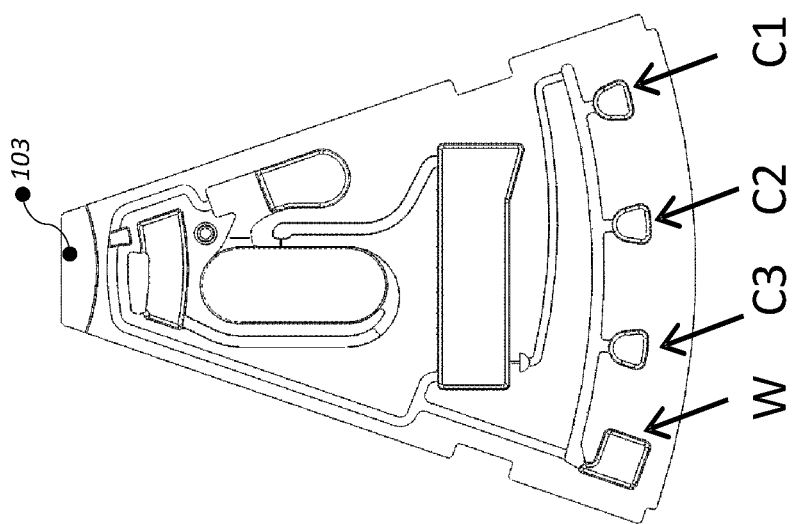
FIG. 13A shows a disposable fluidic centripetal device.

An example fluidic centripetal device 103 is shown in FIG. 13A. This example fluidic centripetal device 103 has three microfluidic containers C1, C2, C3ABC and a waste container W, for a total of 4 containers. In an example embodiment, data acquisition requires less than 1 s per optical channel (i.e. for each fluorophore). The total procedure, including PMT warm-up time and data processing requires less than 10 s to be completed at each PCR cycle.

Example of raw signal acquisition during rotation at 800 RPM of fluidic devices (103) loaded with solutions containing FAM (Carboxyfluorescein) fluorophore is shown on FIG. 13B, by way of example. The signal trace on FIG. 13C represents the raw signal acquired for a complete rotation of 8 fluidic centripetal devices 103 inserted into rotor 102. The signal trace 126 on the bottom graph is a zoom on a single fluidic device signal trace (having 4 containers 104 including container C1, container C2, container C3 and Waste W) and is a fluorescence signal. The square-shaped trace 124 is a representation of data acquisition "windows" generated from the encoder signal. For each microfluidic container 104, only a fraction of the signal contained within a predetermined Region of Interest (ROI) is processed by the Controller electronics 110. This ROI is represented on FIG. 13B by the data processing "windows". This approach enhances signal-to-background ratio and is independent of rotation speed fluctuations.

Figure 9:
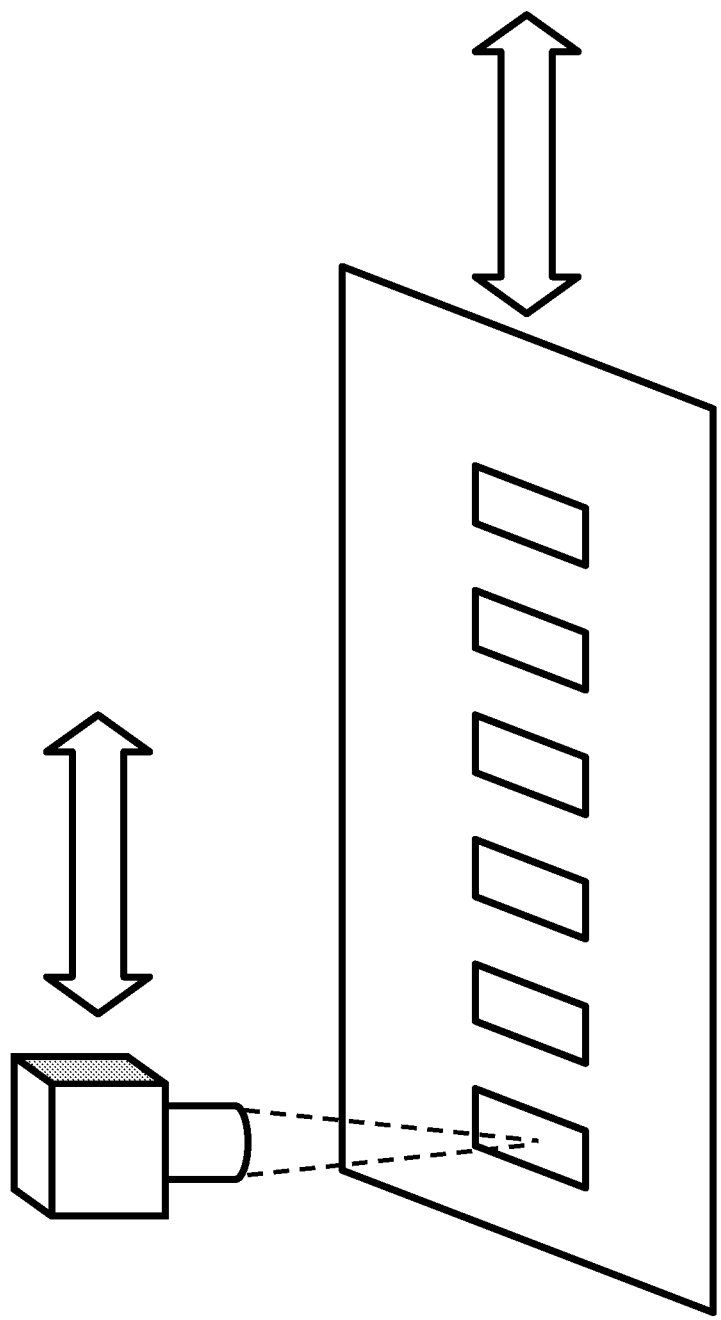
FIG. 9 shows an example embodiment in which the movement between the samples for analysis is linear.

It will be readily understood that the configuration of the test apparatus 100 shown in FIG. 12 is presented by way of example only, and that the optical interrogation devices according to various embodiments of the present invention may be used within different configurations. In additional examples, the movement between the samples for analysis may be linear, that is the structure holding the samples may be scanned linearly with respect to the interrogation device, or the interrogation device scanned linearly with respect to the samples. An example embodiment for such a variant is shown in FIG. 9.

In some embodiments, the interrogation device may be used to detect fluorescence from fluorophores in a sample. As one skilled in the art will readily understand, the concept of fluorescence generally refers to the optical properties of a compound or molecule which absorbs excitation light within a predefined spectral band, the "excitation band/profile", and emits as a result light within a different spectral band, the "fluorescence" or "fluorescent light". A fluorophore is generally understood as a compound or molecule exhibiting such optical properties, usually in a known manner. Optionally, the fluorophore may be covalently or otherwise bound to DNA, antibodies or other molecules or substrates of interest as markers. Examples of fluorophores include amino-acids, proteins, dyes and polymers such as tryptophan, GFP (Green Fluorescent Protein), fluorescein and derivatives such as 6-FAM™, JOE, eosin, Cy3™, rhodamine and derivatives such as ROX, Cy5™, Texas Red®, Quasar® 705, IRDye® 800 and others.

The present devices may be used in a variety of applications where an analyte is excited by light of a given spectral profile and as a result returns light having a different spectral profile, such returned light being generally referred to as luminescence. Embodiments can also be used to detect phosphorescent light from phosphorescing analytes in a sample.

Figure 6A:
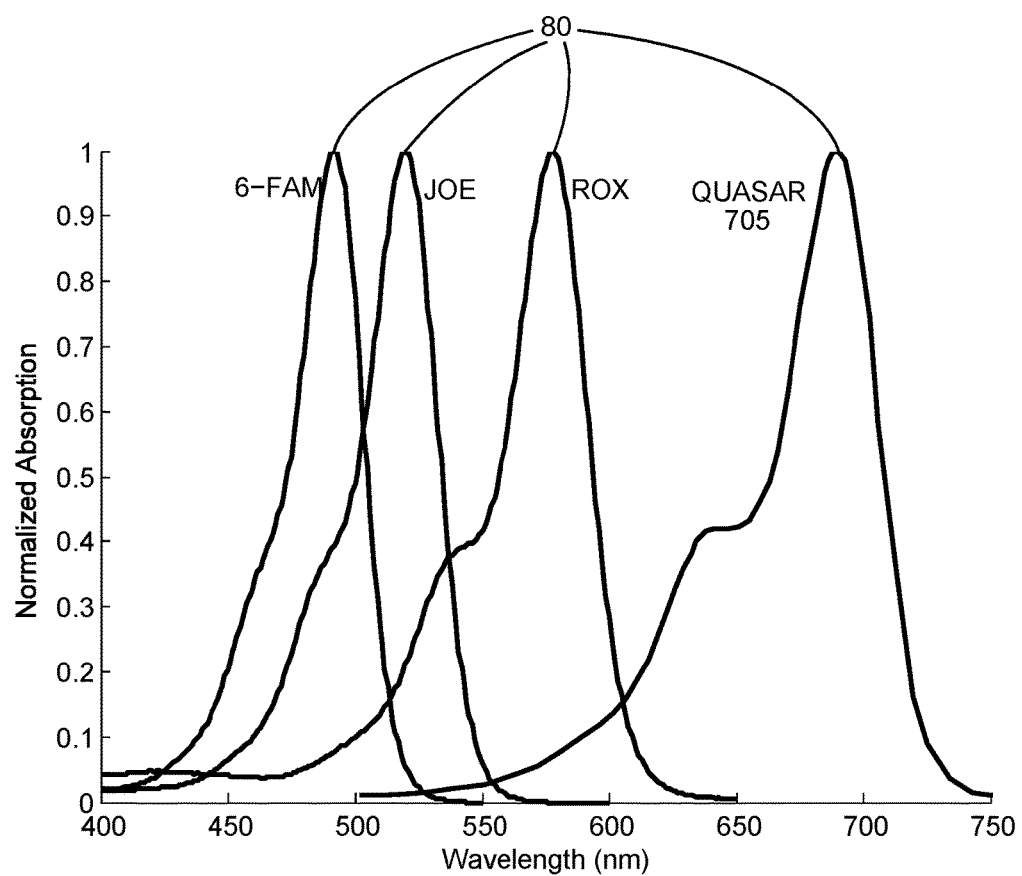
FIGS. 6A to 6B are graphs of absorption and emission spectral profiles of fluorophores, respectively.
Figure 6B:
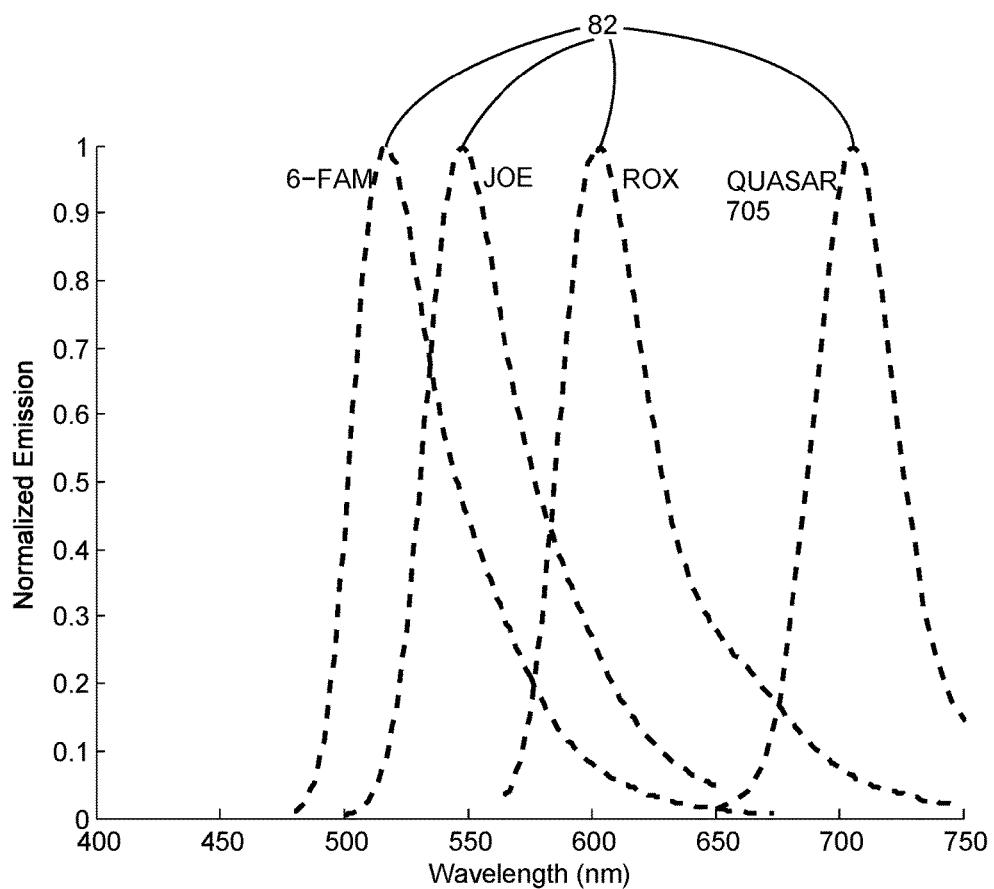
Figure 6C:
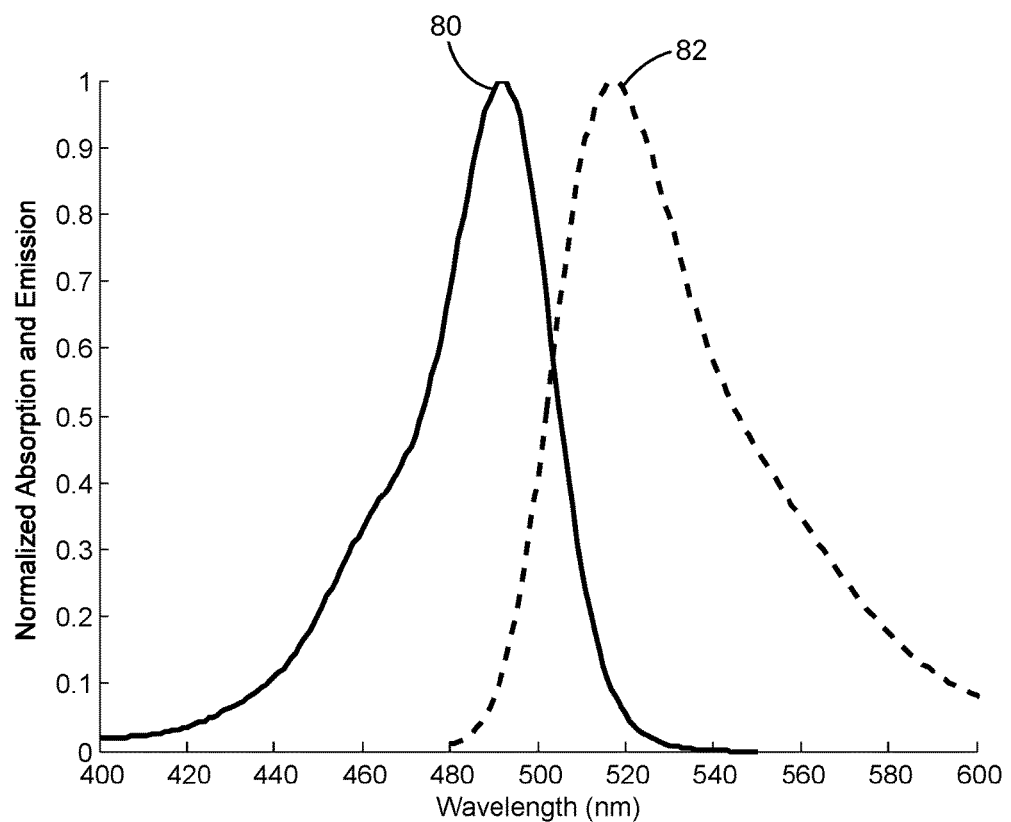
FIG. 6C shows a graph of the normalized absorption and emission for a single fluorophore.

Referring to FIGS. 6A and 6B, there is respectively shown the excitation profile 80 and fluorescence profile 82 of a few fluorophores, presented here by way of example only. FIG. 6C contrasts the excitation and fluorescence profiles 80 and 82 of 6-FAM. As can be seen, both profiles have a slight overlap, but the fluorescence peak is shifted to longer wavelengths with respect to the absorption (excitation) peak. One skilled in the art will understand that embodiments of the present invention are not limited to the specific fluorophores mentioned above and to spectral profiles such as those illustrated herein.

Fluorophores are often used as tools in medical, industrial, forensic and security testing and diagnostic schemes. For example, crime scene experts reveal traces of bodily fluids on surfaces with high contrast by observing fluorescence emitted in the visible spectrum from relatively small quantities of proteins when exposed to invisible ultraviolet illumination. Commercially available methods exist to detect trace amounts of explosives sampled from surfaces or the ambient air using an optical interrogation device and fluorophores, notably an amplifying fluorescent polymer. Fluorescent pigments are commonly incorporated into currency, documents, commercial packaging and other products to mitigate counterfeiting. Finally, medical and laboratory instruments routinely use fluorescence, for example to identify and sort mutated cells from wild type cells, by selectively labeling them with molecular fluorophores having distinct spectral profiles.

The present optical interrogation devices may be used to excite and collect fluorescence from multiple fluorophores in a sample. Depending on the application, the sample can for example be embodied by a volume of an aqueous solution containing fluorophores which may be covalently or otherwise bound to molecules of interest, contained in a transparent plastic or glass vessel or detection cell or the like. Embodiments of the present invention may be used in situations where different fluorophores, having different excitation and florescence spectral profiles, are present in a same sample and need to be interrogated.

Although the present description refers mainly to fluorescence detection, one skilled in the art will readily understand that the embodiments of the present invention may also be used in the context of the observation of other optical phenomena. Applications studying other optical phenomena where a sample is excited by light at one wavelength and emits light at another for example include phosphorescence of molecules such as tryptophan or tetra-iodofluorescein (Erythrosin B, EryB), which have been used to monitor biomolecular mobility of proteins in solution and study the chemical and physical stability of amorphous biomaterials.

Optical Interrogation Device

Figure 1A:
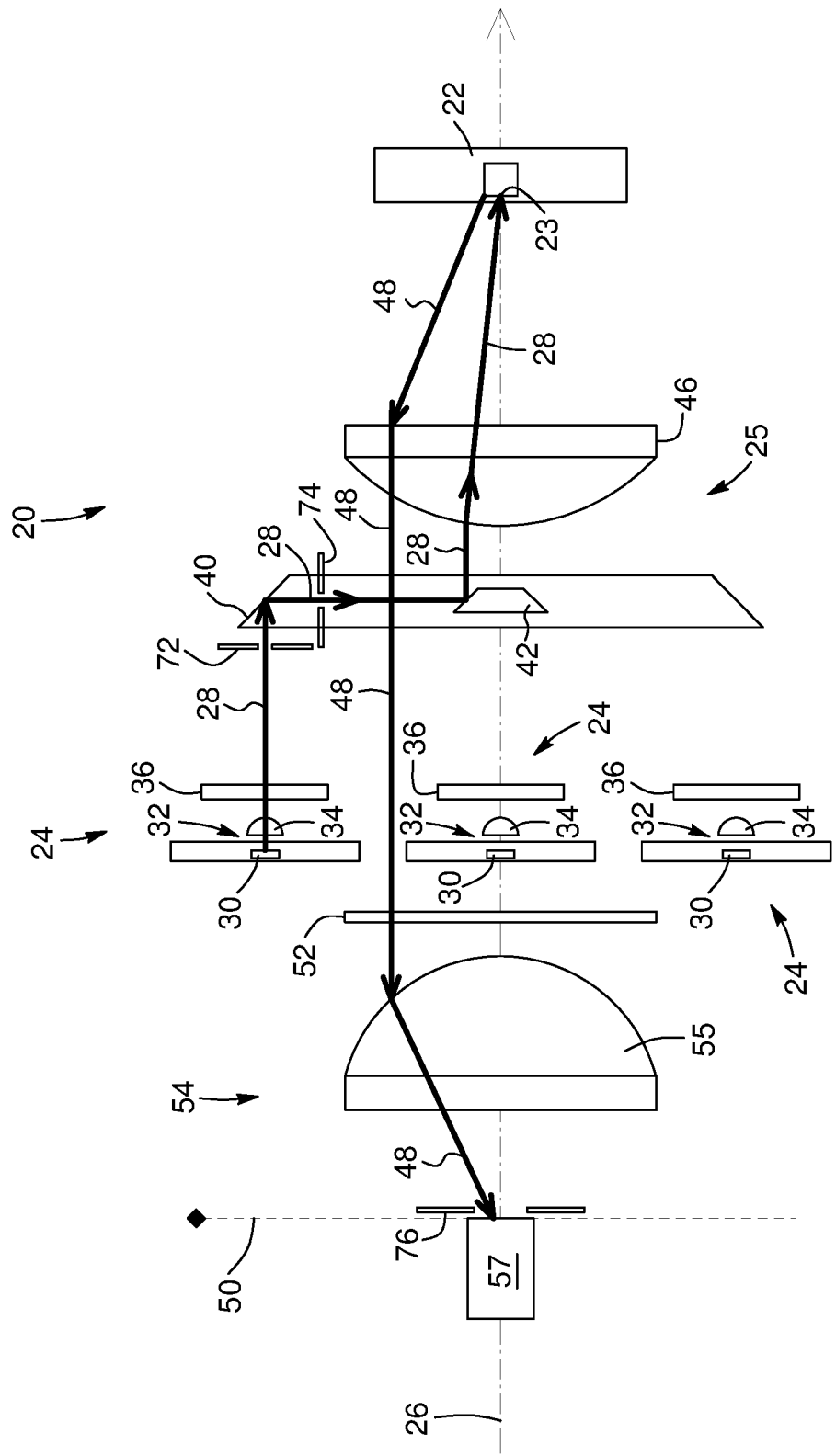
FIGS. 1A and 1B are schematic representations of example optical interrogation devices.

Referring to FIG. 1A, there is shown a schematized representation of elements of an example optical interrogation device 20 for detecting florescence from fluorophores in a sample 22. The optical module is based on an epifluorescence optical configuration in which the different excitation light paths and the luminescence light path are on a same side of the sample. At least one common optical component is used to project excitation light onto the sample and collect fluorescence emission. FIGS. 2 to 5 illustrate an optical assembly embodying such a device, as will be described further below. As explained above, the sample 22 may contain a plurality of different fluorophores with different excitation spectral profiles and fluorescence emission spectral profiles, as shown in FIGS. 6A, 6B and 6C.

Light Source Assemblies

The optical interrogation device 20 first includes a plurality of light sources or light source assemblies 24. A light source assembly typically includes a light source and additional components which accompany the light source. The terms "light source" and "light source assembly" are used interchangeably herein since the person skilled in the art will readily determine if additional components are required for use with the selected light source.

Each light source 24 (or light source assembly) outputs an excitation light beam 28 having individual spectral contents. The individual spectral contents of the light source can be different or similar to that of the other light sources 24. In some embodiments, the spectral content of one or more of the excitation light beams is tailored to a desired application, for example by matching the spectral profile of each excitation light beam 28 to fit within the absorption profile of a target fluorophore while remaining outside of its emission profile. While the spectral contents of different light sources 24 are different, some of these spectral contents may overlap.

In the illustrated example of FIG. 1A each light source assembly includes, successively, a LED 30 generating the corresponding excitation light beam 28, and a spatial filter 32 disposed in the path of the generated light from the LED 30, thereby defining a source object. Advantageously, the size of the pinhole may be designed or adjusted in order to define or vary the size of the source object. Optionally, a condenser lens and/or other optical element or elements (not illustrated) may be included between the LED 30 and pinhole 32 to increase the luminous flux from LED 30 through pinhole 32 and thus the optical excitation light power. Other types of light source may also be considered, such as lasers, laser diodes, incandescent or gas lamps or the like. In other variants, the light sources may be located in proximity or at some distance from the optical interrogation device 20, and the generated light may be fed to the optical interrogation device through fiber optics, lightpipes, waveguides or other means.

Still referring to FIG. 1A, a source lens 34 and/or other optical element or elements collimates the excitation beam 28 from the pinhole 32 in the forward direction to control light dispersion along its path. Optionally, a band-pass filter 36 may be provided within the source assembly 24, so as to spectrally filter the excitation light beam 28 and/or tailor its wavelength profile. The band-pass filter 36 may be interference, diffraction or absorbance based, may include polarizing elements and/or may for example be embodied by a glass disc or rectangle-shaped substrate onto which a coating of material is applied to provide wavelength-specific transmittance.

In an example application, the device is used to interrogate the different fluorophores successively, that is, by activating each light source at a different time. This may for example be achieved by switching the output of an independent constant-current controller for each light source in a timely manner with the help of an embedded microcontroller, itself receiving commands from an overseeing controller or computer, such as the process controller 110 of FIG. 12. Optionally, the electrical power supplied to each source may be controlled in such a way that the optical excitation light power, as sampled by associated optional optical and electronic elements and detectors, reaches a certain desired value in a desired time interval after switching on, and remains stable for the duration of the interrogation and for subsequent interrogations. In an example embodiment, the desired time interval is a short time interval. In some variants more than one of the light sources may be activated at a given time, to simultaneously interrogate different fluorophores.

The optical interrogation device 20 may include at least two and up to any appropriate number of light source assemblies 24. For example, four of such assemblies may be provided, distributed in a circular arrangement. One skilled in the art will understand that this configuration is shown by way of example only. FIGS. 8A, 8B, 8C, 8D and 8E show other possible configurations for the light source assemblies. Within the housing 90, light sources 92 emit excitation light towards the sample-side optics 88 and the sample 86. The fluorescence beam reaches the filter 94, the detector-side optics 96 and finally the detector 98.

Detector

A detector assembly typically includes a detector and additional components which accompany the detector. The terms "detector" and "detector assembly" are used interchangeably herein since the person skilled in the art will readily determine if additional components are required for use with the selected detector.

The optical interrogation device 20 may include a detector 57, or may be connectable to a detector 57 separate from the device. The detector is selected and arranged so as to receive and detect fluorescent (or otherwise luminescent) light from the sample, as will be explained in more detail below. The detector 57 may for example be embodied by a photomultiplier tube (PMT), a photodiode, which may be operated in avalanche mode, a matrix, including a quadrant photodiode, a CCD or CMOS sensor and associated electronics. In the case where the optical interrogation device is used in a test apparatus such as the one shown in FIG. 12, for example embodying a real-time PCR system, the use of a PMT as the detector may be particularly advantageous as it provides the level of sensitivity and a fast response time required for such application.

In one example embodiment, the PMT is selected according to the following requirements:

High sensitivity, Low noise: requirement for low detection limits with typically pWatts of fluorescence collected, PMT provides an intrinsic gain (1M to 10M) and low noise;

Large active area (mm): PCR cuvettes are mm-sized, photocathode is 8 mm in diameter;

Speed: the PCR cuvettes are rotating at 800 RPM, typical PMT $T_r$=few nsec;

Environmental stability: the instrument performs temperature cycling over 50° C., PMTs are less affected by heat than silicon-based detectors.

In an example embodiment, a PMT (photomultiplier tube) detector from the manufacturer Hamamatsu incorporating all high-voltage control circuitry and signal conditioning electronics can be used.

Optical Assembly

The optical interrogation device 20 further includes an optical assembly 25 directing light between the light source assemblies 24, the sample 22 and the detector 57. More specifically, the optical assembly 25 first defines a different excitation light path for each of the excitation light beams 28, from the corresponding light source assembly 24 to a common excitation site 23 on the sample 22. The optical assembly 25 further defines a luminescence light path for the luminescent light 48 from the excitation site 23 on the sample 22 to the detector 57.

The optical assembly defines distinct (separate) and fixed excitation light paths for each of the excitation light beams from the light sources to a common excitation site on the sample. There are no mobile parts in the optical assembly for the excitation light paths. The optical assembly also defines a shared luminescence light path for the luminescent light from the excitation site on sample to the detector. The excitation light paths and the luminescence light path are defined on a same side of the sample. The optical assembly includes sample-side optics projecting the excitation light towards the sample and collecting luminescent light from the sample. The optical assembly provides the sample-side optics in all of the excitation light paths and in the shared luminescence light path.

The excitation light paths are fixed. Indeed, the optical assembly provides a group of components which are permanently set in place in a non-movable manner and together direct, redirect, guide or otherwise affect the excitation light paths within the device. Advantageously, the provision of different fixed light paths within the device alleviates the need for rotating mirrors/filters or other actuated devices for sequentially directing the light (creating the light paths) from the different light sources towards the sample.

The shared luminescence light path is also defined by the optical assembly. An optical component in the luminescence light path could be a support for an actuated filter which could be used for filtering the luminescence light. The filter can be a fixed filter. The filter can be a single-band-pass filter or a multi-band-pass filter.

In the illustrated embodiment of FIG. 1A, the light source assemblies 26 are peripherally distributed about a main axis 26. Each light source assembly 24 projects the corresponding excitation light beam 28 in a forward direction, generally parallel to the main axis 26. In this example, the optical assembly 25 may include a mirror assembly 38 which redirects the light from each light source assembly 24 towards the sample 22. In one embodiment, the mirror assembly 38 includes two components: an outer reflective element 40 and an inner reflective element 42. The outer reflective element is disposed in a path of the excitation beams 28 from the light source assemblies 24 and inwardly redirects the same, that is, deviates the excitation beams towards the main axis 26 of the device. It will be understood that the light path between the outer and inner reflective elements 40 and 42 need not be at a right angle to these elements and need not be a direct path. The outer reflective element 40 may for example be embodied by a ring-shaped conical mirror having an inner surface 41 facing the light source assemblies (see for example FIG. 3). In other embodiments the outer reflective element 40 may be embodied by individual mirrors each paired with one of the light source assemblies. The inner reflective element 42 receives the excitation light beams 28 from the outer reflecting element 40 and redirects the same in the forward direction, towards the sample 22. In one example, best seen in FIG. 5, the inner reflective element 42 may be embodied by a pyramidal mirror disposed within the perimeter of the outer reflective element 40 and which may be disposed concentrically thereto.

Various combinations and configurations of optical elements may be devised to embody the inner reflective element 42. In some implementations, mirrors embodying the outer or inner reflective elements may be manufactured by depositing reflective layers on optical components of the device.

Figure 1B:
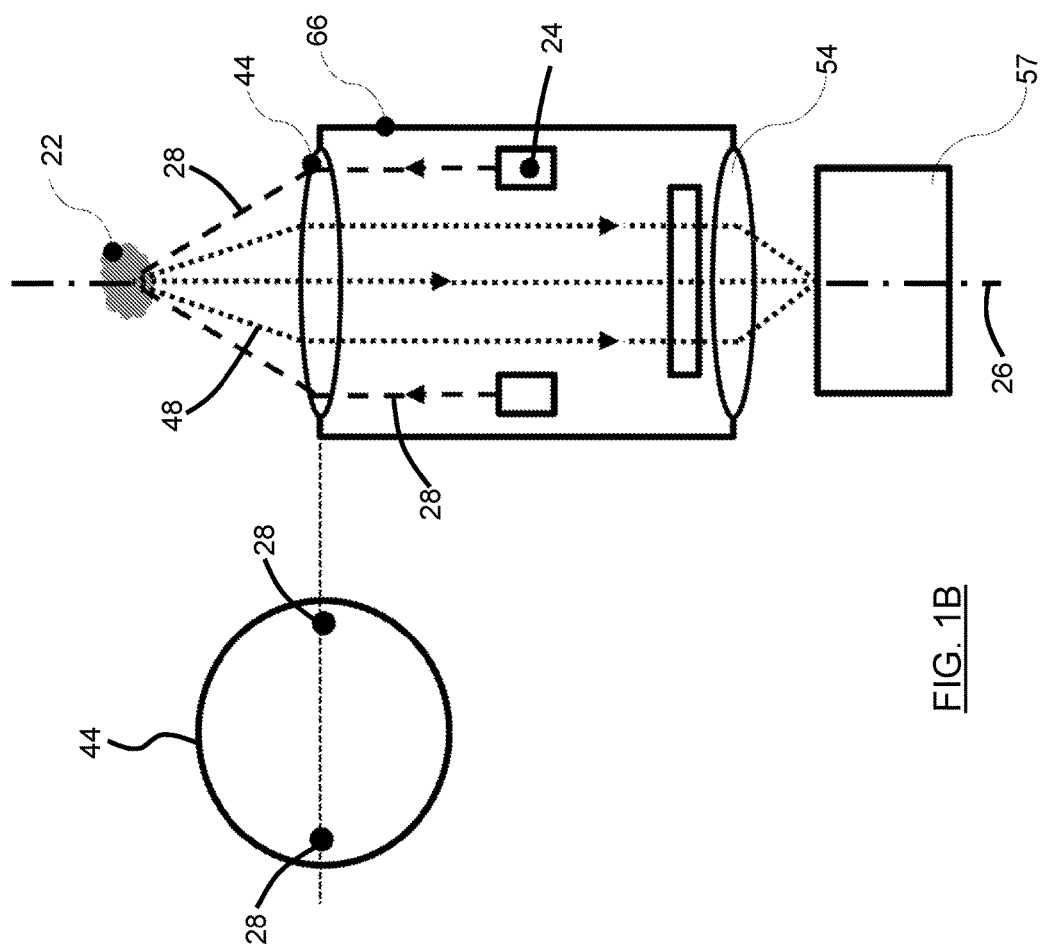

In the illustrated embodiment of FIG. 1A, the light source assemblies are distributed peripherally to the main axis 26 of the optical interrogation device, and the excitation light beams are redirected inwardly such that they are outputted towards the sample close to the main axis 26. The luminescence from the sample circulates back into the device along a luminescence light path. Other configurations may however be envisioned. For example, with reference to FIG. 1B, in an alternative embodiment the excitation light beams follow a peripheral excitation light path before being redirected towards the sample by sample-side optics 44.

FIGS. 8A to 8E illustrate variations of optical assemblies where different optical components and combinations are used to define the excitation and luminescent light paths.

Figure 8C:
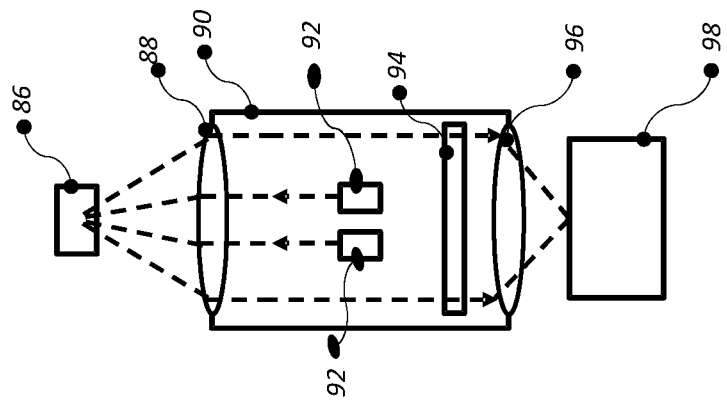
FIGS. 8A to 8E are schematic illustrations of variants of the exemplary embodiments described above using different configurations for the light source assemblies.
Figure 8B:
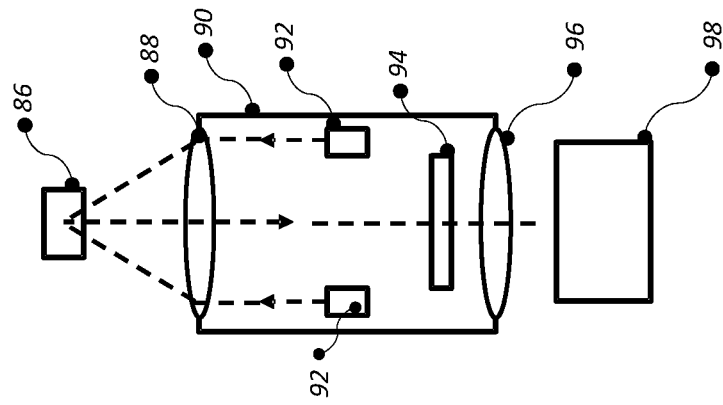
Figure 8A:
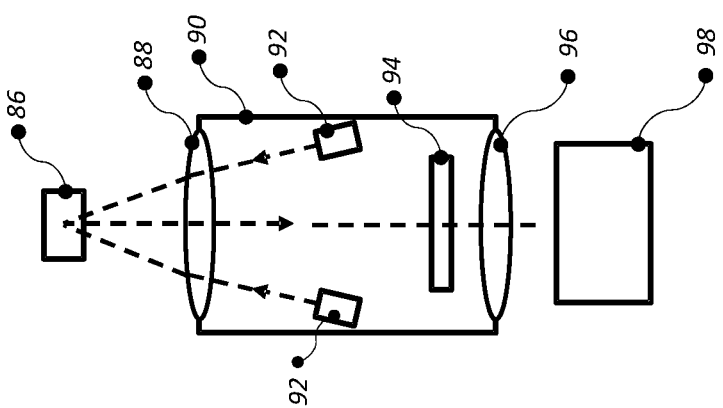
Figure 8E:
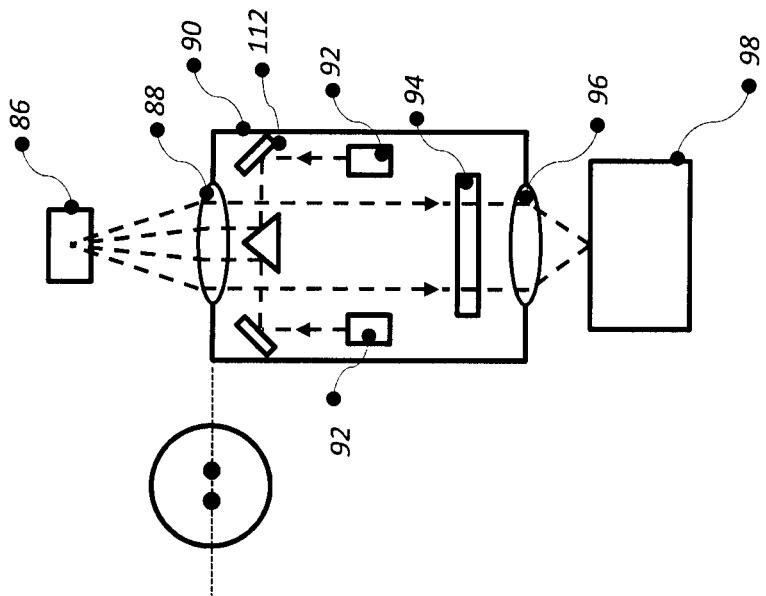
Figure 8D:
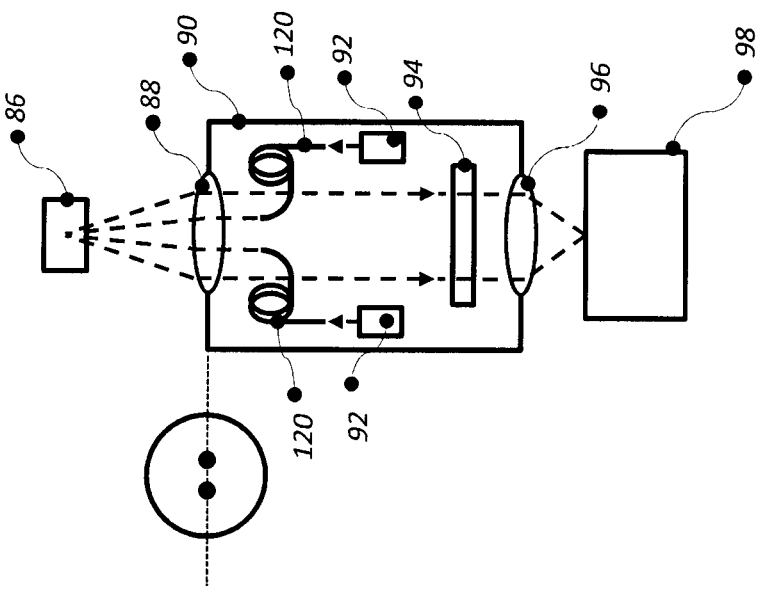

In some embodiments, the light source assemblies may each include a waveguide, such as an optical fiber, to guide the excitation light beam. This is illustrated schematically in FIG. 8D. Each light source assembly includes, successively, a LED generating the corresponding excitation light beam and a first lens pinhole disposed in the path of the generated light from the LED to collimate the excitation light. A band pass excitation filter is then provided followed by a second lens which focalizes and couples the filtered excitation light from the LED onto the waveguide 120. The waveguide may be a 500 μm optical fiber, for example. At the output of each waveguide, a microlens collimates the excitation light. Each waveguide projects its collimated light into the sample-side optics lens which focalizes and projects it into an excitation volume located in the sample. Each excitation light at a different excitation wavelength is projected onto the same excitation volume in the sample. In FIG. 8E, reflective optics 122 are used to create the light beam paths.

In some embodiments, spatial filters may be provided in the path of the excitation light beams 28 in order to limit the physical size of the travelling beams and reduce noise associated with stray light (FIG. 1A, elements 72, 74). As one skilled in the art will readily understand, the light emitted from LED sources is divergent, the emitted beams having an increasingly broadening cross-section along their propagation axis. This effect can be limited by placing spatial filters at various locations along the path of the beams.

Figure 7:
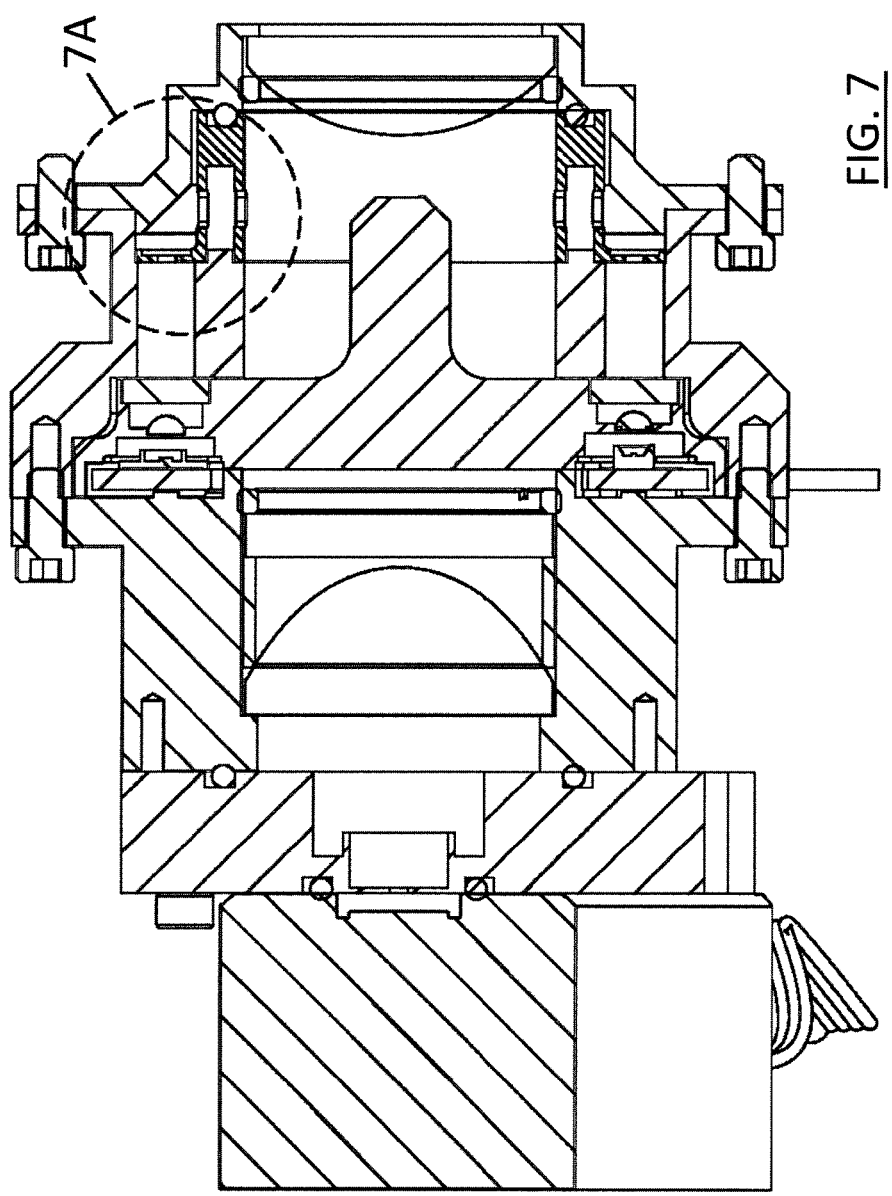
FIG. 7 is a cross-sectional side view of an example optical assembly defining a fluorescence device.
Figure 7A:
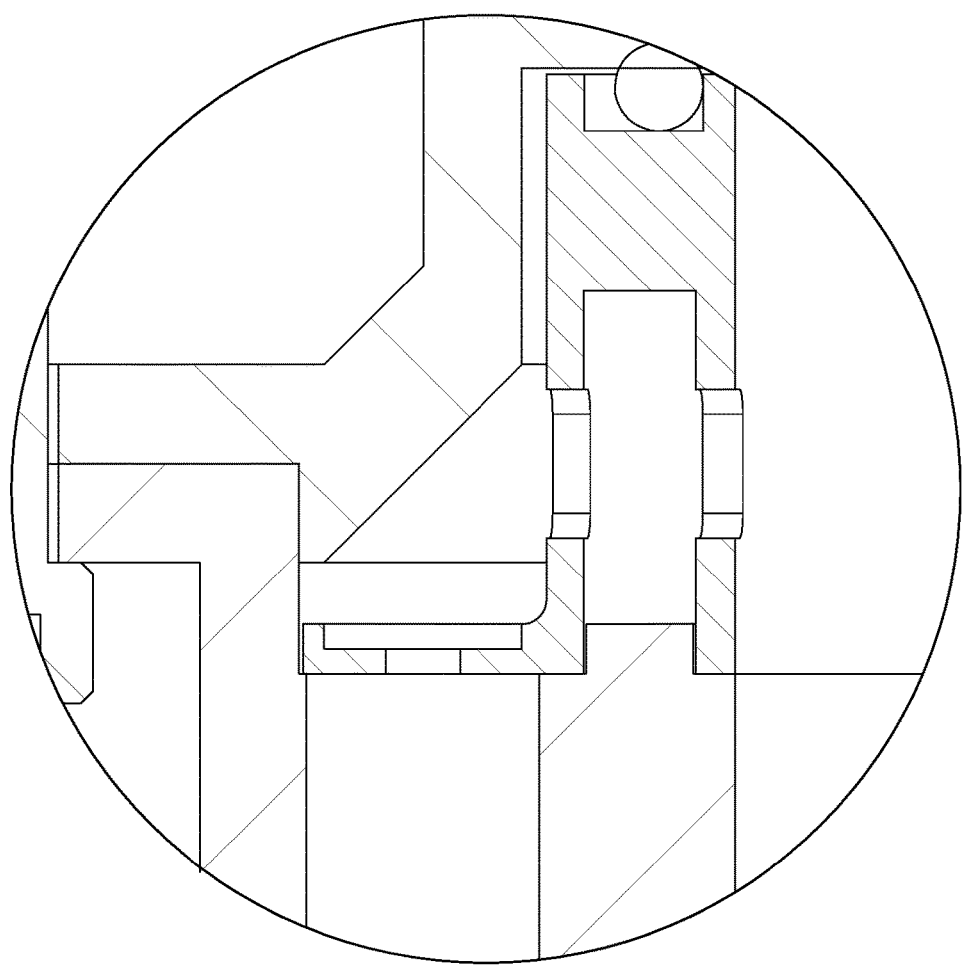
FIG. 7A is an enlarged view of section 7A of FIG. 7.

Referring to FIGS. 1A and 7A, in one embodiment a first spatial filter 72 is positioned in the path of each excitation light beam slightly upstream from the outer reflecting element 40. For example, the first spatial filter 72 may be embodied by a blocking plate provided with an opening therein. The size of the opening may be selected so that the dimension of excitation beam 28 allowed through the first spatial filter 72 is substantially smaller that the dimension of reflecting element 40. The blocking plate may substantially absorb and/or substantially diffuse non-specularly the blocked portions of the excitation beam to reduce the presence of stray reflections.

A second spatial filter 74 may be disposed in the path of the excitation light beams 28 after reflection by the outer reflecting element. The second spatial filter 74 may for example be embodied by a similar blocking plate provided with an opening therein. The size of the opening may be selected so that the dimension of excitation beam 28 allowed through the second spatial filter 74 is substantially smaller that the dimension of reflecting surface 62 (facet) (see FIG. 4) of the inner reflective element 42. The blocking plate substantially absorbs and/or substantially diffuses non-specularly the blocked portions of the excitation beam to further reduce the present of stray reflections 40.

Other spatial filtering elements may be disposed along the path of excitation beam 28 to provide further filtering and stray light control/rejection. The number, position and configuration of spatial filters greatly depends on the excitation source spatial profile (ex. a well collimated laser beam will require less (or no) spatial filtering than a highly divergent LED source. It also depends on the excitation source spectral profile and the S/N requirements of the application. For example, a light source having a spectral profile corresponding to the peak sensitivity of the detector, or a light source used in combination with a fluorophore having a small Stokes shift (its excitation and detection spectral bands being very close) will generally require more spatial filtering to achieve good performances.

The optical interrogation device 20 may include sample-side optics 44 directing the excitation light beams 28 from the inner reflective element 42 towards the sample 22. Preferably, the sample-side optics includes at least one converging lens 46 focusing the excitation light beams 28 from the different light source assemblies 24 at a same location 23 on the sample 22, thereby allowing excitation light going through each pinhole 32 to be projected at or about an excitation plane in the sample 22. Preferably, all or most of the excitation light beams 28 are converged on a same region of the sample 23, or on a small volume thereof which is sufficiently small for the purpose of the target application. Any number of other or additional optical components could be provided as part of the sample-side optics 44. As will be readily understood by one skilled in the art, the above described configuration and variants thereof provide a convenient control on the size and shape of the excitation volume.

Within the excitation volume of the sample 22, a given fluorophore will absorb the light from one of the excitation light beam 28 if the spectral contents of this light beam at least overlap with the excitation spectral profile of the fluorophore. It will then emit fluorescent light 48 according to its fluorescence profile. Fluorescence is usually emitted from a bulk solution in an isotropic fashion, and therefore at least some of the fluorescent light 48 will be emitted back towards the interrogation device 20 and collected by the converging lens 46. From this direction the converging lens 46 collimates the collected light so that it propagates as a collimated or near-collimated beam in a rearward direction through the interrogation device 20.

Generally, the components of the device 20 described above are shaped and disposed so as to be as un-obstructive as possible to the rearward propagating fluorescent light 48. A least a portion of the fluorescent light 48 travelling rearward through the device reaches a detection plane 50, which is the location where light is collected for detection. In the illustrated embodiment, the detection plane 50 extends behind the plane of the light source assemblies 24. Preferably, an output spectral filter 52 is disposed in the path of the luminescent light 48 prior to the detection plane 50. The output spectral filter 52 excludes the undesired spectral contents, such as those from the excitation beams 28. In this manner, parasitic reflections or scattering of the excitation beams 28 directed towards the detection plane 50 will be filtered out, reducing noise and/or background signal. The output filter may be interference, diffraction or absorbance based, and/or may for example be embodied by a glass disc or rectangle-shaped substrate onto which a coating of material is applied to provide wavelength-specific transmittance.

Detector-side optics 54 outputting the filtered fluorescent light 48 for detection may be provided. For example, the detector-side optics 54 may include an output lens 55 to converge the fluorescent light 48 towards the detection plane 50. Other optical components may additionally or alternatively be provided. For example, an output spatial filter 76 may be provided in the path of the fluorescent light, for example proximate to the detection plane 50. The output spatial filter 76 may for example be embodied by a blocking plate provided with a suitably sized opening, for example equal or smaller to the projected image of the excitation beam footprint at the sample 22. Advantageously, the provision of such a filter can greatly reduce the amount of stray background radiation reaching the detector, improving the signal-to-noise ratio. In other variants, a combination of spectral and spatial filtering may be provided using a diffractive element (example a transmission grating or prism), appropriate detector-side optics 54 and a spatial filter 76 made of suitably sized openings or waveguides with their positioning and sizing at the imaging plane defining the spectral bands of interest.

Figure 10C:
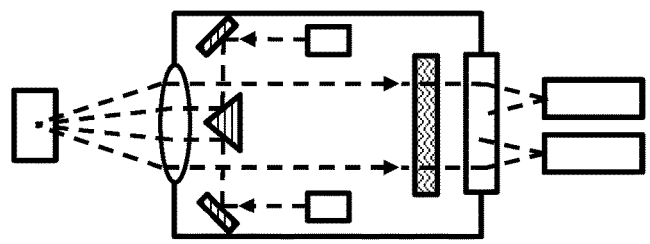
FIGS. 10A to 10H are schematic illustrations of variants of the exemplary embodiments described above using different filtering configurations.
Figure 10B:
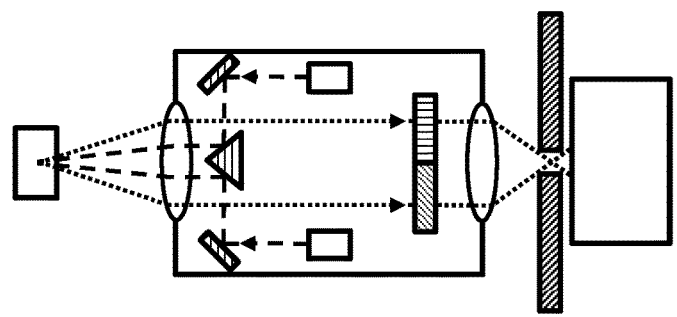
Figure 10A:
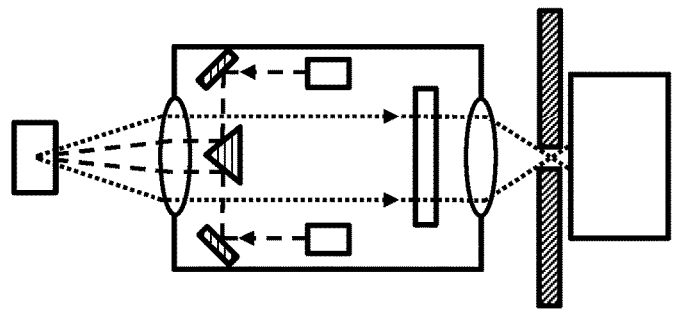
Figure 10F:
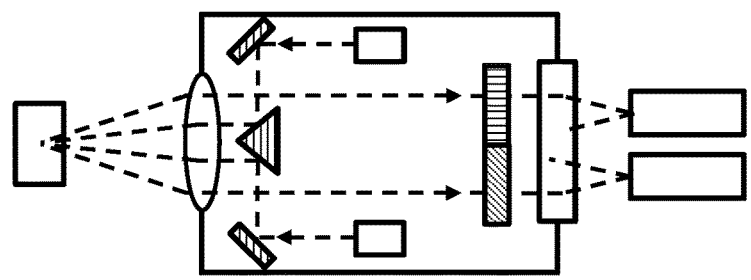
Figure 10E:
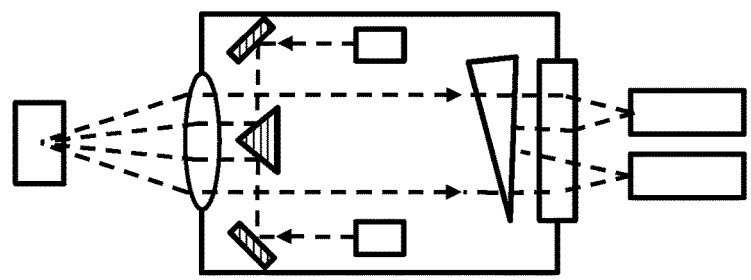
Figure 10D:
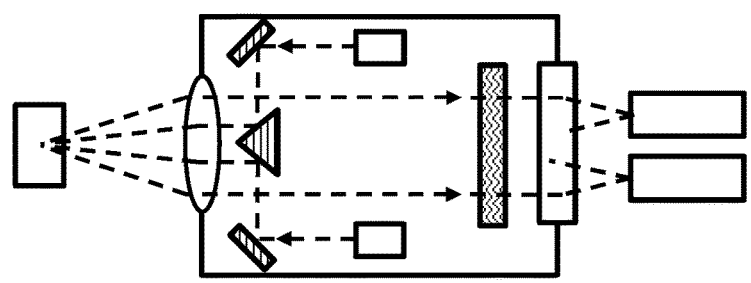

FIGS. 10A to 10H show different configurations for the filtering of the luminescent light beam and the coupling of the luminescent light with the detector. In some embodiments, the detector 57 is provided at the detection plane 50 and directly coupled to the detector-side optics 54 to receive the fluorescent light 48 therefrom. This is the embodiment shown in FIG. 10A for a sequential excitation/detection scheme (one wavelength after another) single detector, single (multiband) filter. In alternative embodiments, the fluorescent light 48 may be guided by a waveguide such as an optical fiber between the detection plane 50 and the detector 57. In a single-detector configuration, multiple filters, either sequential or parallel, may be provided in the path of the luminescent light. This is shown in FIG. 10B where multiple filters are used for a sequential detection scheme, single detector embodiment. Multiple-detector configurations can also be envisioned, such as shown in FIGS. 10C to 10F. In FIG. 10C, multiple detectors are used simultaneously (simultaneous excitation/detection scheme)

with a spatial distribution of spectral content. In FIG. 10D, multiple detectors are used simultaneously with a spatial distribution of spectral content using transmission grating. In FIG. 10E, multiple detectors are used simultaneously with a spatial distribution of spectral content using a refractive material such as a prim. In FIG. 10F, multiple detectors are used simultaneously with a spatial distribution of spectral content using bandpass interference filters.

In one embodiment, the measurement method involves LED-based excitation of a dye and the simultaneous detection of the emitted fluorescence by the PMT detector. To excite multiple fluorophores in a sample, multiple LEDs are sequentially activated. Since LED emission is spectrally broad, the use of a narrowband interference filter allows for the tailoring of the emission spectral profile to the absorption characteristics of a selected fluorophore and the transmission characteristics of the multiband emission filter. A single pentaband detection filter can be used. Because the OM configuration uses a multiband emission filter, there is a risk associated with the excitation of more than one fluorophore (optical cross talk). In that case, emission from multiple fluorophores will be detected without spectral selectivity. The emitted fluorescence collected by the OM from the PCR cuvettes is spectrally filtered using a multiband interference filter located in front of the PMT to remove undesired wavelengths. Each of the filter's transmission bands corresponds to the emission spectra of the selected fluorophores.

Figure 10H:
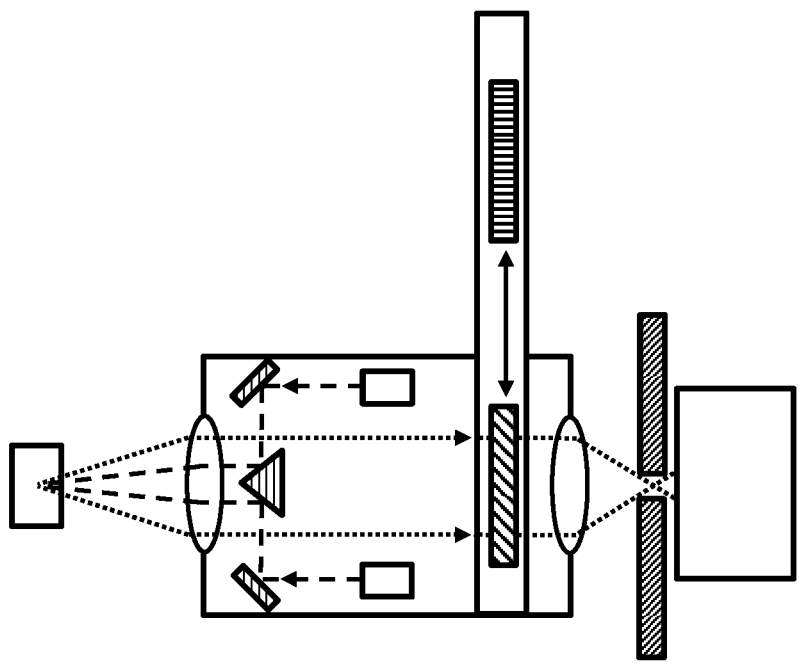
Figure 10G:
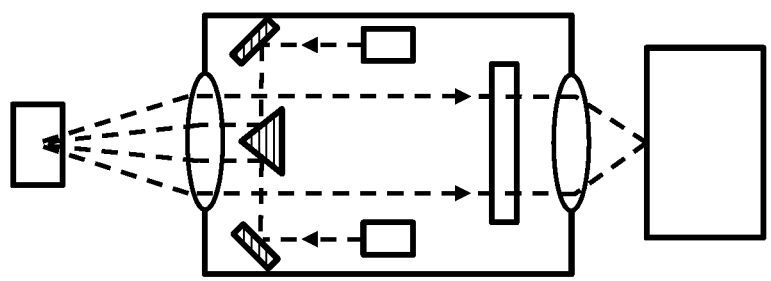

In some embodiments shown in FIGS. 10G and 10H, the detection filter could be provided by actuated detection filters. The actuated filter assembly could include a carousel. The measurement method would still involve LED-based excitation of a dye and detection of the emitted fluorescence by the PMT detector through an appropriate narrowband detection filter. The latter would be sequentially placed in the detection path. Excitation/detection of all channels would be performed sequentially.

The advantages of this embodiment are numerous: less cross talk in the best case scenario, better control on excitation/detection bands, better control on fluorophore/filter selection, flexibility for the number of dyes used. Indeed, the excitation/detection channels could be implemented using commonly available fluorophores. The fluorophores could be obtained from a single supplier such as Biosearch, for example. For example, fluorophones which are excited and which emit between 485 nm and 705 nm could be used.

This embodiment presents some disadvantages including a longer detection time and a moving part which is subject to malfunctioning after prolonged use of the apparatus.

Exemplary Embodiments

Referring to FIGS. 2 to 5, 7 and 7A there is shown, by way of example, optical assemblies which may embody the optical interrogation device 20 described above. Preferably, the optical assembly is designed to facilitate its manufacture and limit or negate the necessity for precise alignment of its optical components.

Figure 4:
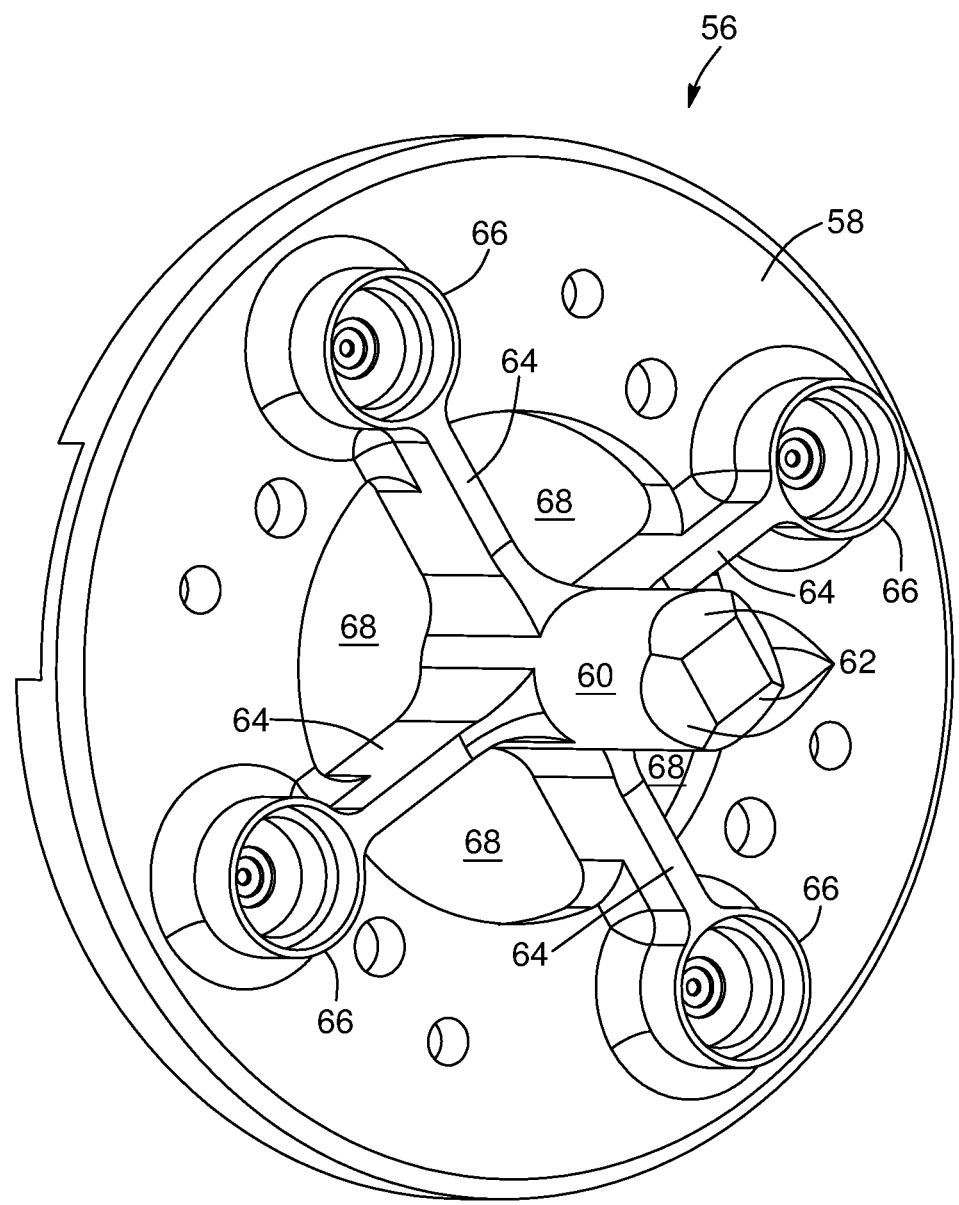
FIG. 4 is an isometric view of an example support structure of the device of FIG. 2.
Figure 5:
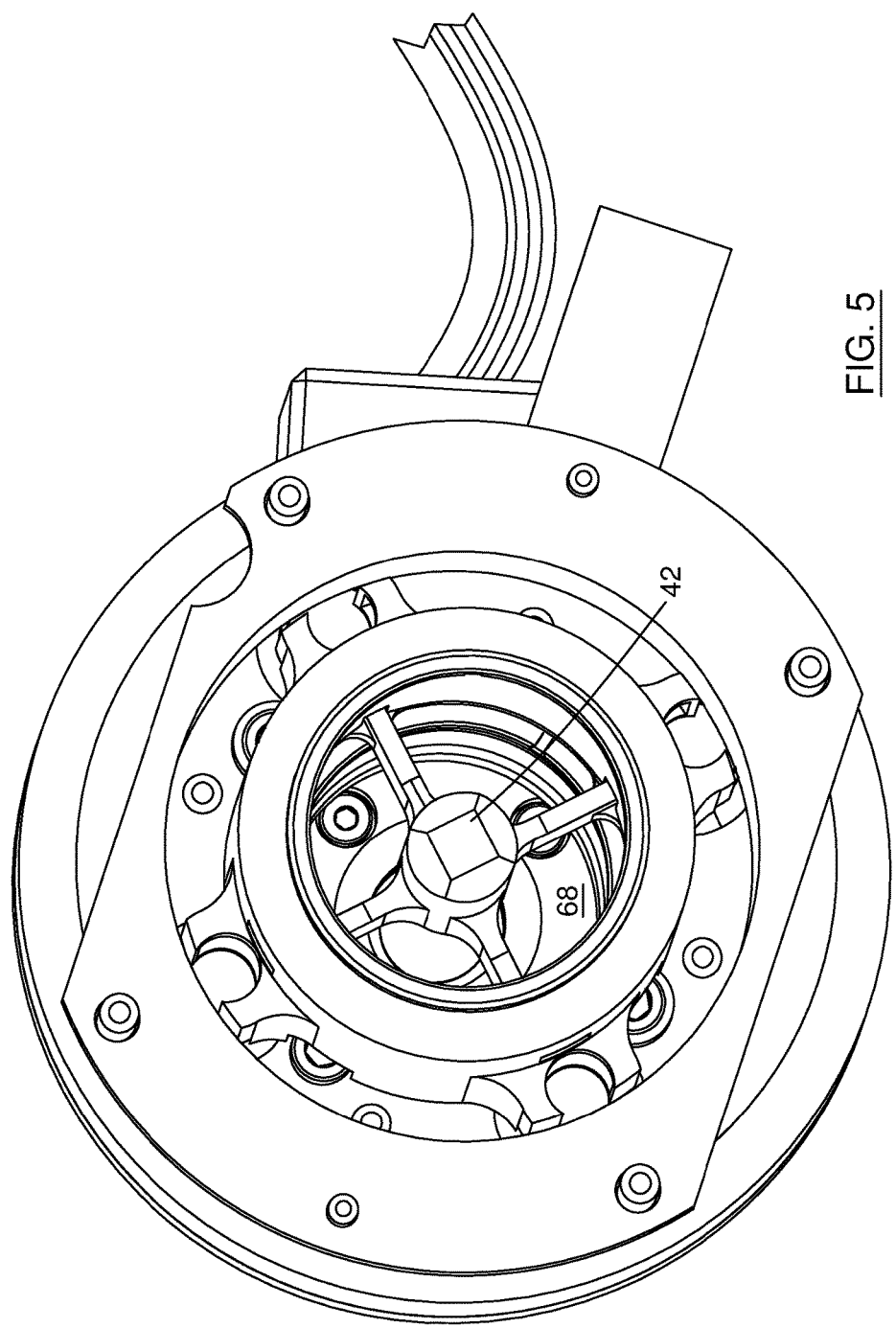
FIG. 5 is a front view in partial transparency of the device of FIG. 2.

In these embodiments, amongst various components, a support structure 56 for the light source assemblies 24 is provided. The support structure 56 may have one or more peripheral frame elements 58 on which the light source assemblies are mounted. In the illustrated element the peripheral frame element is generally disk-shaped, as best seen in FIG. 4. The support structure may further include a central column 60, projecting perpendicularly from the plane defined by the peripheral frame element 58. The central column supports the inner reflecting element 42. In the illustrated embodiment, the extremity of the central shaft 60 projecting away from the peripheral frame element 58 is machined to define a pyramidal shape having a plurality of facets 62 positioned and oriented to redirect the excitation light beams as explained above. Each facet 62 may be manufactured from and/or coated with a reflective material such as nickel, aluminum, silver, gold or a combination thereof.

The support structure may further include a plurality of connecting ribs 64 which connect the peripheral frame element 58 and the central shaft 60. In the illustrated embodiment, the connecting ribs 64 each form housing 66 at the peripheral extremity thereof to receive therein one of the light source assemblies. Preferably, the connecting ribs 64 are shaped to occupy limited space around the central shaft 60 to define one or more light passages 68 between them, for allowing the luminescent light therethrough.

The support structure or any structure of the device may further include or provide accommodation for one or several light baffles 70 (FIG. 2) featuring light absorbing/light diffusing surfaces and/or geometry, the purpose of which is to prevent or at least diminish an importance of transmission, specular reflection or scattering of stray light beyond the light paths intended by design. Such baffles may for example be manufactured or coated with light absorbing/light diffusing materials.

Further, any transmissive, reflective or absorptive surface may be designed and/or coated in such a way that it features wavelength-specific transmittance, reflectance and/or absorbance to aid in obtaining the desired excitation and detection spectral profiles, reducing the amount of transmitted, reflected and/or scattered stray light, or achieving any other purpose related to the desired function of the system.

The optical assembly 25 may be based on other configurations involving various types of mirrors, lenses, prisms, lightpipes, baffles and other optical elements.

FIG. 14 shows exploded views of an example optical module for use with a test apparatus such as shown in FIG. 12. The Optical Module (OM) and its components can be divided into 5 sub-assemblies as shown in FIG. 14. The Distal Tube (FIG. 14A) contains a reflective surface that directs LED light into the module and a lens that directs excitation light to the PCR cuvettes and collects emitted fluorescence. The PMT tube (FIG. 14B) contains the multiband filter and the lens that focusses the fluorescence light onto the PMT detector. The LED Optics assembly (FIG. 14C) also contains a reflective surface that directs LED light into the module as well as LED excitation filters and LED beam conditioning components (pinholes & miniature lenses). Excitation filters and mini-lenses are glued to the LED Optics assembly body for robust and stable operation. The LED Printed Circuit Board (FIG. 14D) supports the LED chips and provides the electrical interface with the LED drivers on the Optics Controller board. Finally, the detector module (FIG. 14E) contains a voltage-output PMT and a mating plate for interfacing with the OM. All sub-assemblies are mounted using fine-thread screws and O-rings between interfaces guarantee a light-tight assembly.

Figure 15B:
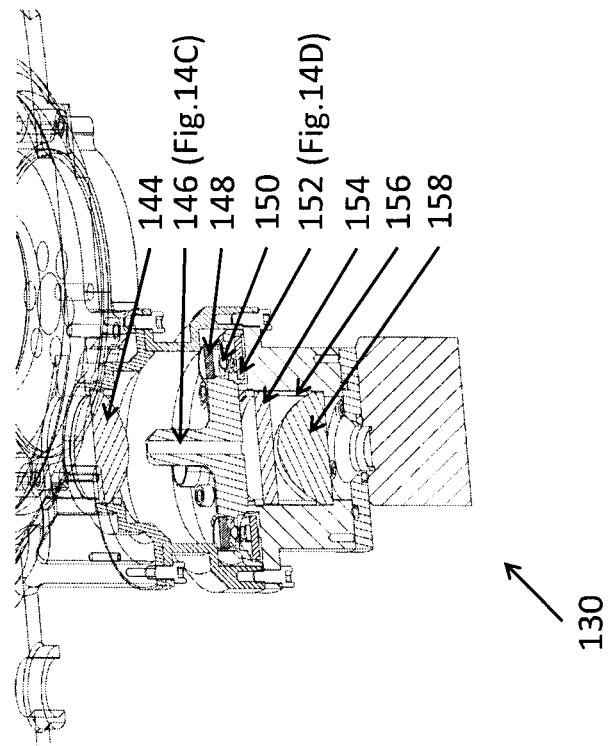
FIG. 15B shows a cross sectional view of the assembled module of FIG. 14.
Figure 15A:
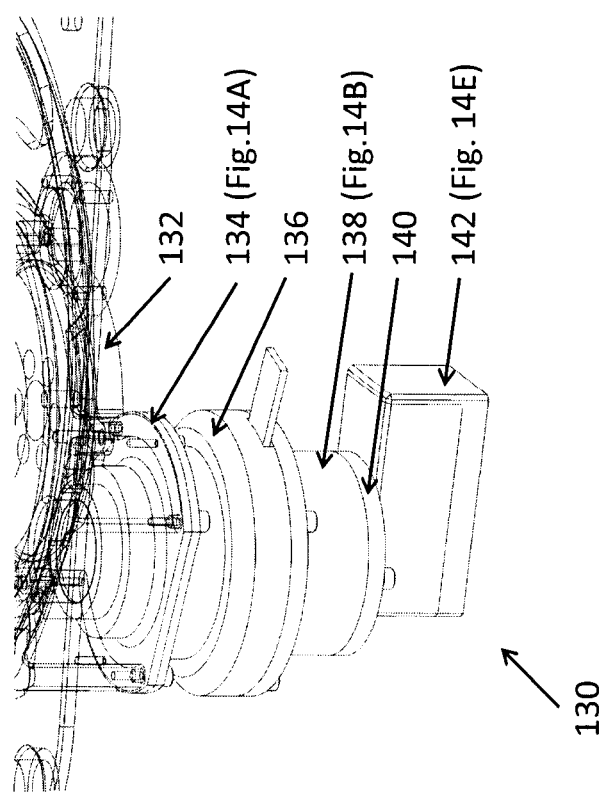
FIG. 15A shows an assembled view of the example optical module of FIG. 14

FIG. 15A shows an assembled view of the example optical module of FIG. 14 and FIG. 15B shows a cross-sectional view of the assembled module of FIG. 14. The OM 130 is mounted to the bottom plate of the instrument 132. Tight fabrication tolerances on the OM, on the bottom plate and on the microfluidic holder provide an alignment-free assembly (X,Y,Z) of the OM with respect to the PMCD cuvettes, thanks to a depth of field in the mm range. The distal tube 134 (exploded in FIG. 14A), the central tube 136, the PMT Tube 138 (exploded in FIG. 14B), the PMT Plate 140, the PMT Detector 142 (exploded in FIG. 14E), the Condenser lens 144, the LED Optics 146 (exploded in FIG. 14C), the LED Excitation filter 148, the LED optics 150, the LED PCB 152 (exploded in FIG. 14D), the Pentaband Fluorescence Filter 154, the Spacer 156 and the Plano-Convex Lens 158 are shown in FIGS. 15A and 15B.

Figure 16:
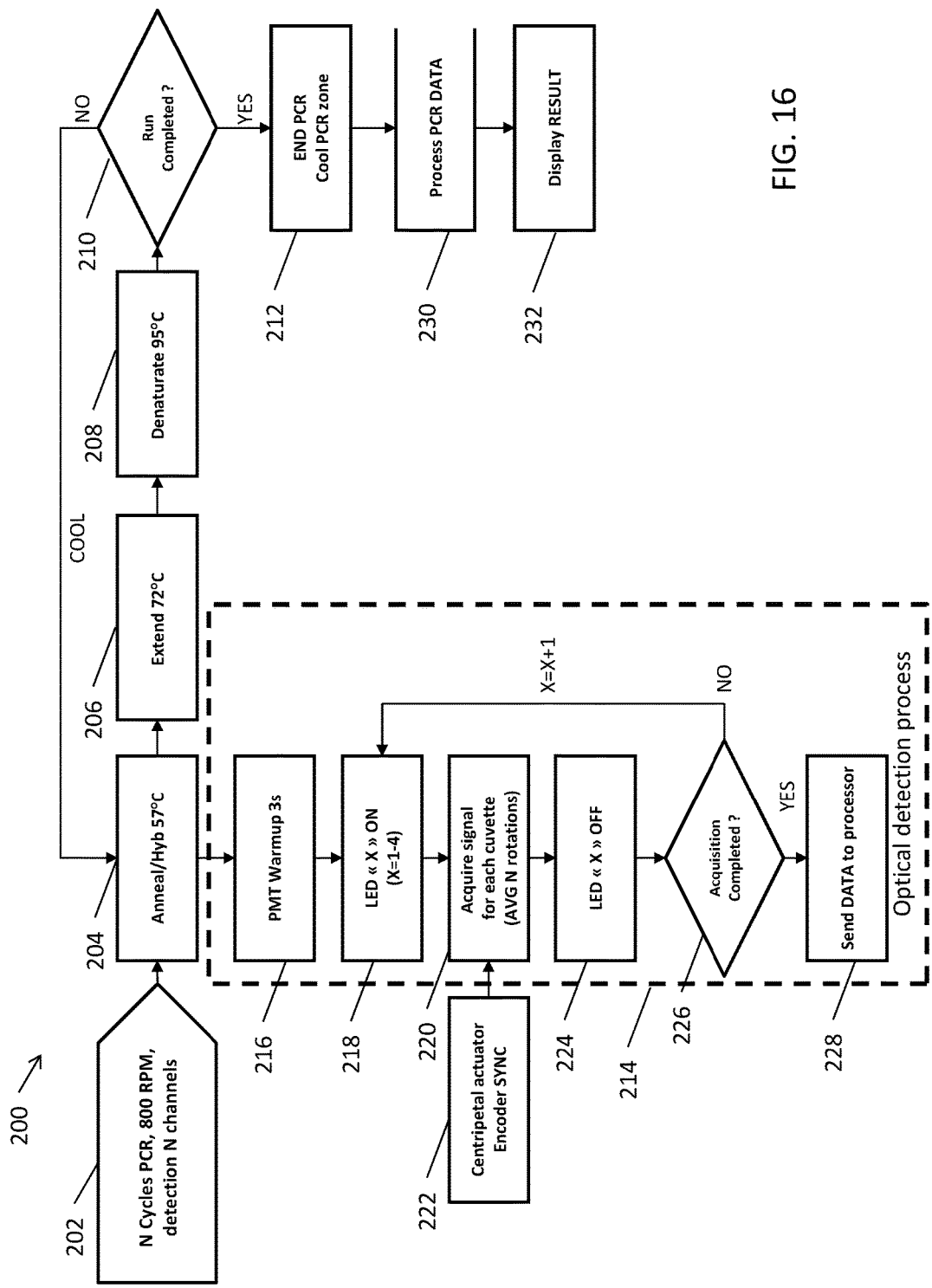
FIG. 16 is an example optical module workflow.

FIG. 16 is an example optical module workflow 200. Optical measurements are performed at each PCR cycle 202, as illustrated in FIG. 16. When cooling is performed (annealing step 204) and the temperature reaches 57° C. C for a duration of 20 seconds, the Instrument Processing & Control Unit (PCU) triggers the Optics Controller and the signal acquisition procedure 214 is performed in parallel with the temperature cycle which includes an extend step 206 to 72° C. C for a duration of 2 seconds and a denaturate step 208 to 95° C. C for a duration of 1 second. The temperature cycle is repeated until the run is completed 210. When the run is completed, the PCR is ended 212. In the optical detection process 214, a PMT stabilization time of 3 seconds is provided 216 at the beginning of each measurement cycle. LEDs are sequentially activated 218 during the measurement procedure. The signal is acquired for each cuvette 220 and synchronized 222 with the centripetal actuator encoder. The LED is turned off 224. Once fluorescence measurements are completed 226, data is sent to the PCU 228 and the Optics Controller waits for the next trigger. This procedure is repeated at each PCR cycle. Once PCR cycles are completed, data is further processed 230 and analyzed. The results can be displayed 232.

Experimental Results

Example 1

As mentioned above, the optical interrogation device according to example embodiments described above may be useful for real-time PCR systems, for example through a test apparatus such as shown in FIG. 12.

Figure 11A:
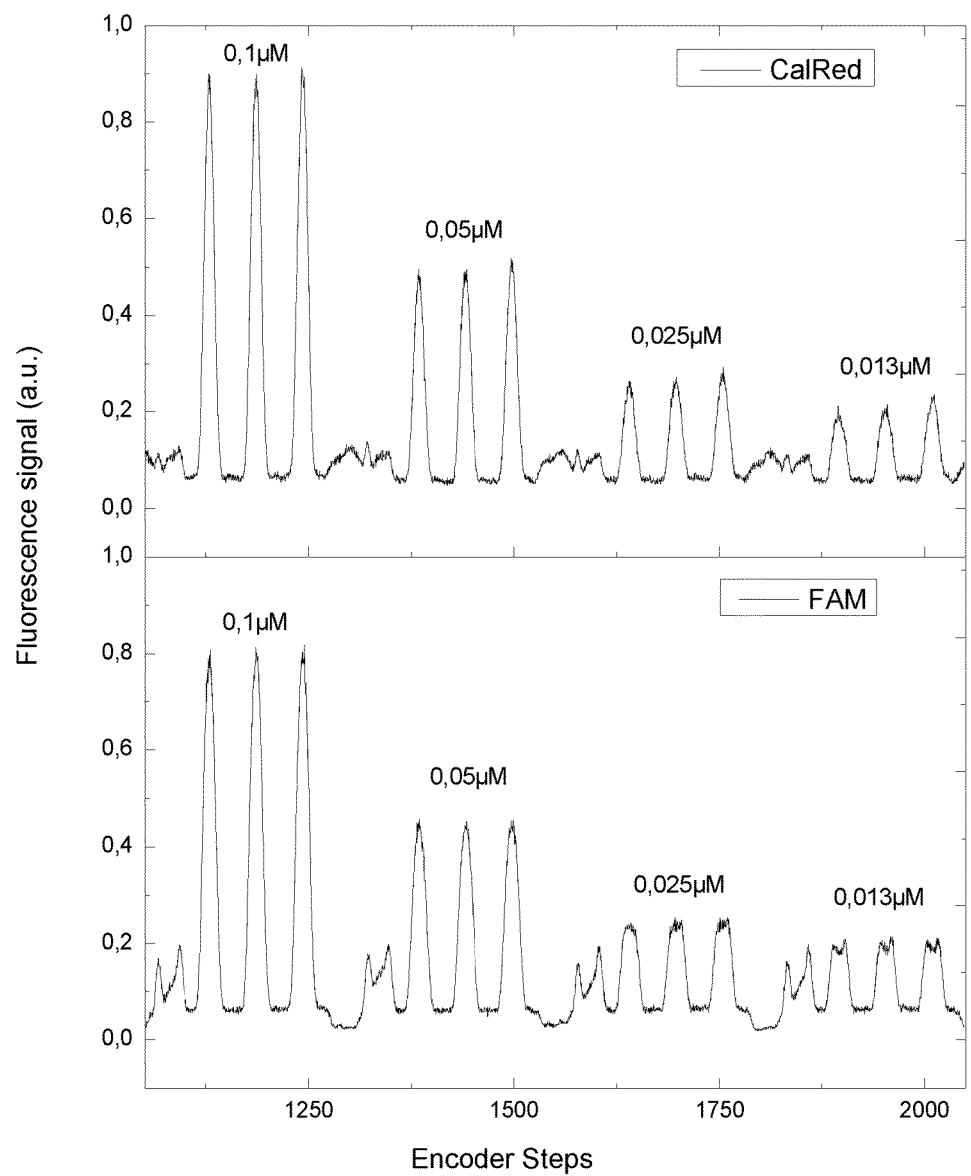
FIG. 11A shows calibration results for two fluorophores detected using an instrument incorporating an example optical interrogation device.
Figure 11B:
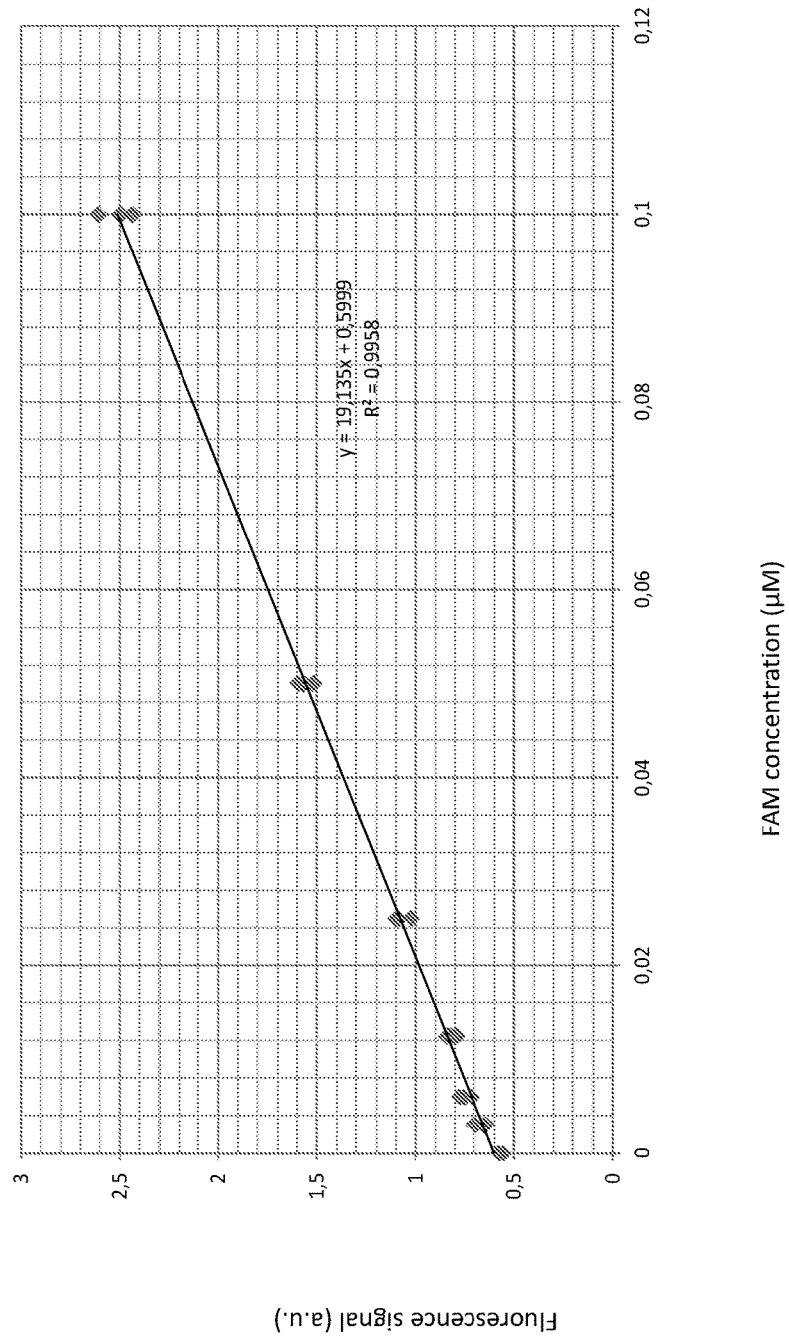
FIGS. 11B and 11C show the corresponding calibration curves.
Figure 11C:
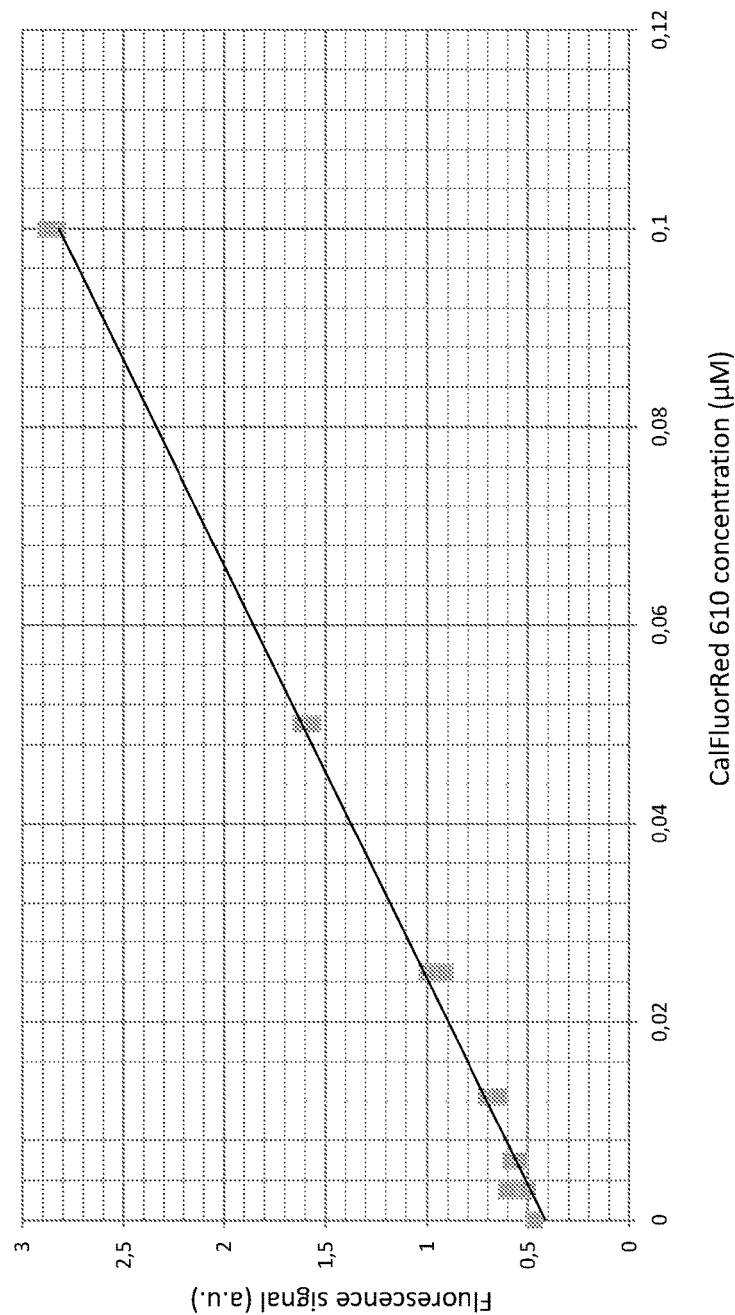

FIG. 11A shows results obtained through such a system for fluorescence detection of two dyes (FAM and CAL Fluor® Red 610 Dye) on a rotating disc. FIGS. 11B and 11C show the calibration curves for the system used. The samples contained both dyes. Sequential detection was performed during rotation at 800 RPM. The recorded signals are overlapped, showing the advantage of using an actuator with an encoder as a sync signal and the overlap of intersecting excitation beams within the sample. The FAM dye has an excitation wavelength of 485 nm and a detection wavelength of 520 nm. The $LOD_{3\sigma}$ is 2.3 nM and the $LOQ_{10\sigma}$ is 7.7 nM. The CAL Fluor® Red 610 Dye has an excitation wavelength of 560 nm and a detection wavelength of 607 nm. The $LOD_{3\sigma}$ is 3.0 nM and the $LOD_{10\sigma}$ is 10.1 nM.

Example 2

Fluorescence figures of merit (Limit of detection (LOD) and Limit of Quantification (LOQ)) were obtained for an optical module with Blue, Green, Red and Near Infrared (NIR) excitation channels and Pentaband detection filter.

The Optical Control Board (OCB) included the LED controller system and electronic adjustment of LED power. Table 1 shows LEDs and filters used for each optical channel and Table 2 shows dye used for this evaluation. Roithner products are available from Roithner Lasertechnik GmbH and Semrock products are available from Semrock, Inc.

TABLE 1

Optical channels configuration

| Optical Channel | LED | Filter |
|---|---|---|
| Blue | Roithner APG2C1-490 | Semrock FF02-485/20 |
| Green | Roithner APG2C3-530 | Semrock FF02-560/25 |
| Red | Roithner APG2C1-650 | Semrock FF02-650/13 |
| NIR | Roithner APG2C1-740 | Semrock FF01-740/13 |
| Detection | | Semrock FF01-440/521/607/694/809 |

TABLE 2

Dye selection

| Optical Channel | Dye | $\lambda_{max}$, Excitation | $\lambda_{max}$, Emission |
|---|---|---|---|
| Blue | FAM | 495 nm | 520 nm |
| Green | CAL Fluor ® Red 610 Dye | 590 nm | 610 nm |
| Red | Cy5 | 646 nm | 662 nm |
| NIR | Alexa 750 | 749 nm | 775 nm |

For each dye, eight (8) DFCDs were loaded with solutions of concentration from 0 to 0.2 μM (0, 0.003, 0.006, 0.012, 0.025, 0.05, 0.1 and 0.2 μM). Fluorescence was measured for all DFCDs (Disposable Fluidic Centripetal Device) in all channels and calibration curves relating fluorescence measurements to dye concentration were obtained.

DFCDs loaded with PCR matrix only ("0 μM" concentration; 10 mM Tris-HCl pH 8.0, 50 mM NaCl, 5 mM MgCl2) were then used to quantify background noise and standard deviation on background noise and thus, to evaluate LOD and LOQ. Crosstalk was evaluated by measuring dye fluorescence in other channels than channel of interest (i.e. at other excitation wavelengths).

Fluorescence vs. concentration data was obtained for all dyes in all optical channels. Table 3 presents slopes obtained for all optical channels.

TABLE 3

Slopes, coefficient of determination $R^2$, LOD & LOQ for all channels

| Channel | Dye | Slope (mV/μM) | $R^2$ | $LOD_{3\sigma}$ (nM) | $LOQ_{10\sigma}$ (μM) |
|---|---|---|---|---|---|
| Blue | FAM | 13.76 | 0.996 | 7.3 | 24.3 |
| Green | CAL Fluor ® Red 610 Dye | 7.06 | 0.980 | 6.6 | 22.0 |
| Red | Cy5 | 17.76 | 0.997 | 1.6 | 5.4 |
| NIR | Alexa 750 | 9.58 | 0.925 | 3.5 | 11.8 |

Linear fluorescence calibration curves were successfully obtained for all channels.

For the optical design used in this experiment, crosstalk occurs when the excitation spectra of a dye overlaps with the excitation bands of other optical channels, making it difficult to isolate the fluorescence response of one specific dye. From the results presented above, one can see that crosstalk occurs between optical channels. To quantify (and ultimately compensate) crosstalk, calibration curves were acquired for each dye at every excitation wavelength available.

Table 4 and Table 5 show fluorescence compensation matrices relating fluorescence to dye concentrations in the presence of crosstalk. The normalized compensation matrix was obtained by computing the ratio of the slope of all dyes in one channel vs. the slope of the dye of interest in that particular channel. Crosstalk was considered significant only for slopes having a coefficient of determination $R^2>0.50$.

In a configuration with Blue/Green/Red/NIR channels and FAM/CAL Fluor Red 610/Cy5/Alexa 750 dyes, optical crosstalk occurs in the green channel in presence of Cy5 dye ($R^2=0.94$) and in the red channel in presence of Alexa 750 dye ($R^2=0.92$). As shown in Table 6, none of the other dyes showed significant crosstalk (i.e. $R^2<0.50$). Crosstalk was 5% or less for all other channel/dye combinations.

TABLE 4

Fluorescence compensation matrix (Slopes in mV/µM) for FAM, CAL Fluor ® Red 610 Dye, Cy5, and Alexa 750 in Blue, Green, Red and NIR optical channels.

|  | Blue | Green | Red | NIR |
| --- | --- | --- | --- | --- |
| FAM | 13.76 | 0.09 | 0.09 | 0.23 |
| CAL Fluor ® Red 610 Dye | 0.66 | 7.06 | 0.13 | 0.17 |
| Cy5 | 0.38 | 1.04 | 17.76 | 0.23 |
| Alexa 750 | 0.51 | 0.20 | 2.73 | 9.58 |

TABLE 5

Normalized fluorescence compensation matrix (%) for FAM, Cal Fluor Red 610, Cy5, and Alexa 750 in Blue, Green, Red and NIR optical channels.

|  | Blue | Green | Red | NIR |
| --- | --- | --- | --- | --- |
| FAM | 100% | 1% | 0% | 2% |
| CAL Fluor ® Red 610 Dye | 5% | 100% | 1% | 2% |
| Cy5 | 3% | 15% | 100% | 2% |
| Alexa 750 | 4% | 3% | 15% | 100% |

TABLE 6

Coefficient of determination (R2) for FAM, CAL Fluor ® Red 610 Dye, Cy5, and Alexa 750 in Blue, Green, Red and NIR optical channels.

|  | Blue | Green | Red | NIR |
| --- | --- | --- | --- | --- |
| FAM | 0.996 | 0.036 | 0.121 | 0.379 |
| CAL Fluor ® Red 610 Dye | 0.174 | 0.980 | 0.213 | 0.248 |
| Cy5 | 0.370 | 0.941 | 0.997 | 0.388 |
| Alexa 750 | 0.380 | 0.065 | 0.915 | 0.925 |

Example 3

The protocol and results for the typical multiplex detection of two targets within the same DFCD are described in this example.

DFCD disposables were prepared with a PCR mixture dispensed and dried in each of the 3 cuvettes (refer to FIG. 13A). Table 7 describes the final PCR mixture composition in each cuvette following resuspension with a sample.

TABLE 7

Final PCR mixture composition in each cuvette

| MasterMix Component | Concentration (in each cuvette) | Unit |
| --- | --- | --- |
| Sag59 (primer) | 0.4 | µM |
| Sag190 (primer) | 0.4 | µM |
| cfbSag-T1-A1 (*S. agalactiae* target probe, FAM-labeled) | 0.2 | µM |

TABLE 7-continued

Final PCR mixture composition in each cuvette

| MasterMix Component | Concentration (in each cuvette) | Unit |
| --- | --- | --- |
| ciGBS-T1-F2 (Int. Control probe, Cal Fluor Red 610-labeled) | 0.2 | µM |
| Tris-HCl pH 9.0 | 10 | mM |
| KCl | 50 | mM |
| Triton X-100 | 0.1 | % |
| BSA | 3.3 | mg/ml |
| MgCl2 | 5 | mM |
| dNTPs | 0.2 | mm |
| GoTaq enzyme | 1.15 | Units |
| Excipient | 1.3 | % |
| Internal Control | 500 | DNA copies |

Primer and probe sequences are described in Table 8.

TABLE 8

Primer and probe sequences.

| Name | Sequences |
| --- | --- |
| Sag59 | TTTCACCAGCTGTATTAGAAGTA |
| Sag190 | GTTCCCTGAACATTATCTTTGAT |
| cfbSag-T1-A1 | CCCAGCAAATGGCTCAAAAGC |
| ciGBS-T1-F2 | TCTCTTGGATCTTGCTCATGCCCC |

The internal control consists of purified genomic DNA from *Bacillus subtilis* (gene thyA modified strain). The thyA gene of *Bacillus subtilis* subsp. *subtilis* str. 168 (BGSCID 1A1) has been modified by homologous recombination. Amplification of this internal control sequence is accomplished with the same primers as those of the *S. agalactiae* cfb gene but is detected using a different probe labelled with CalFluorREd 610. The concentration of the internal control has been adjusted to 500 genome copies per PCR reaction.

DFCD disposables were loaded with 1000 copies of a positive control and centrifuged at 3000 RPM to bring the sample volume into the cuvettes. 50 PCR amplification cycles were performed for this experiment using the following parameters: annealing at 57° C. for a duration of 20 seconds; extension at 72° C. for a duration of 2 seconds and denaturation at 95° C. for 1 second. Optical detection was performed during thermal cycling as described in FIG. 16.

Data Analysis

Data generated by the instrument was processed offline using the algorithm described below. Out of the 50 PCR cycles that were performed, only the first 45 cycles of the PCR amplification were necessary for data processing.

Data from each run were logged in a file which contains rotational speed, temperature and fluorescence measured through the instrument procedure.

Background Subtraction

A linear regression (slope and y-intercept) was used to remove background from data sets prior to data analysis. This background can be caused by multiple phenomena such as residual fluorescence of the quenched dye, difference in DFCD transparency and/or scatter, background fluorescence from DFCD materials or reagents, background noise, labeled probes degradation, etc.

Figure 17A:
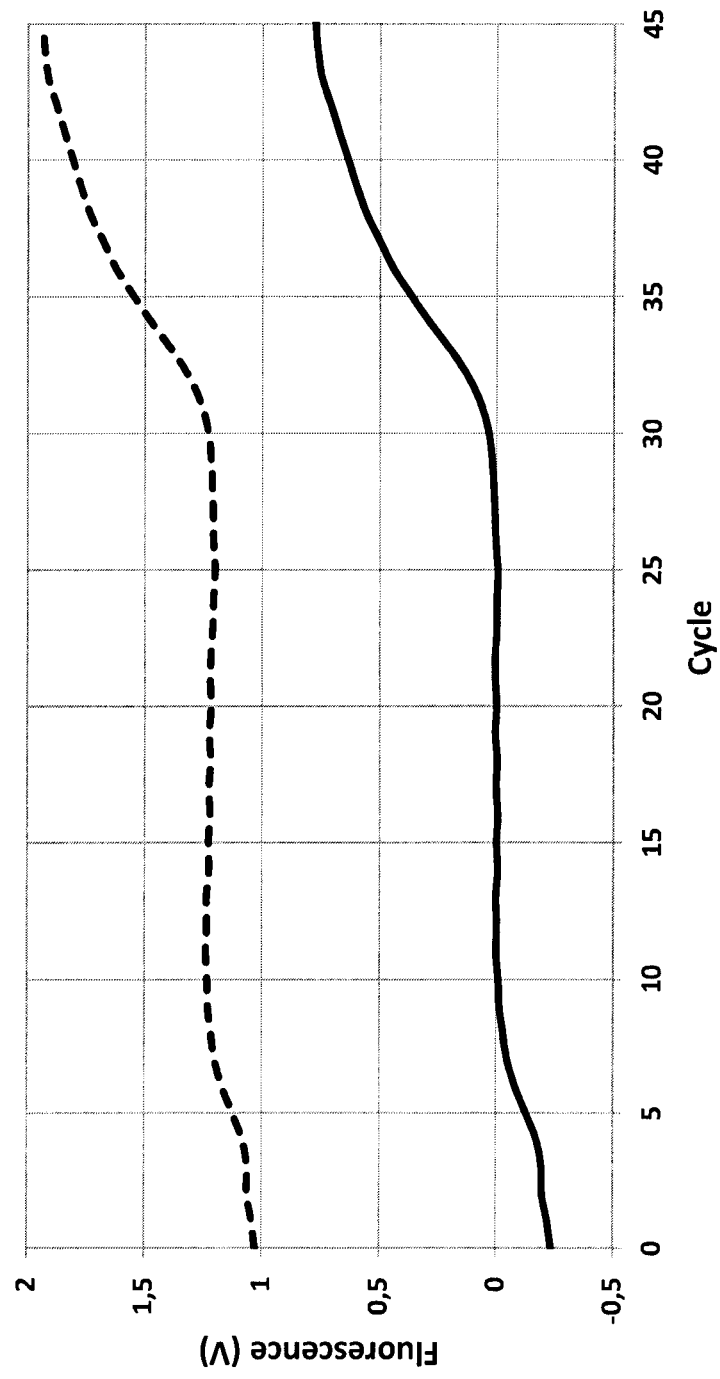
FIG. 17A shows example results for fluorescence readings during real-time PCR amplification of nucleic acids, with and without background subtraction.

Fluorescence measurement from cycles 15 to 25 were used to compute the background correction for each sample. These data points were chosen since they are late enough for the fluorescence to be steady and early enough so that the PCR amplification has not produced enough target yet to be detectable. FIG. 17A illustrates fluorescence data without (top curve) and with (bottom curve) background subtraction.

Sigmoidal curve-fitting (SCF) was used to perform the relative quantification of the target concentration in positive samples. The point of inflexion (maximum of the second derivative) was used to determine the Cycle Threshold (Ct) with great precision. This method was chosen since no arbitrary threshold for Ct has to be determined prior to experimentation.

A sigmoidal curve of the following form was used to fit fluorescence data:

$$F_{SCF} = \frac{a}{1 + e^{-(C-C_0/b)}}$$

where $F_{SCF}$ is the fluorescence computed through the sigmoidal curve-fitting model, C is the cycle and a, b and $C_0$ are the SCF parameters.

Figure 17B:
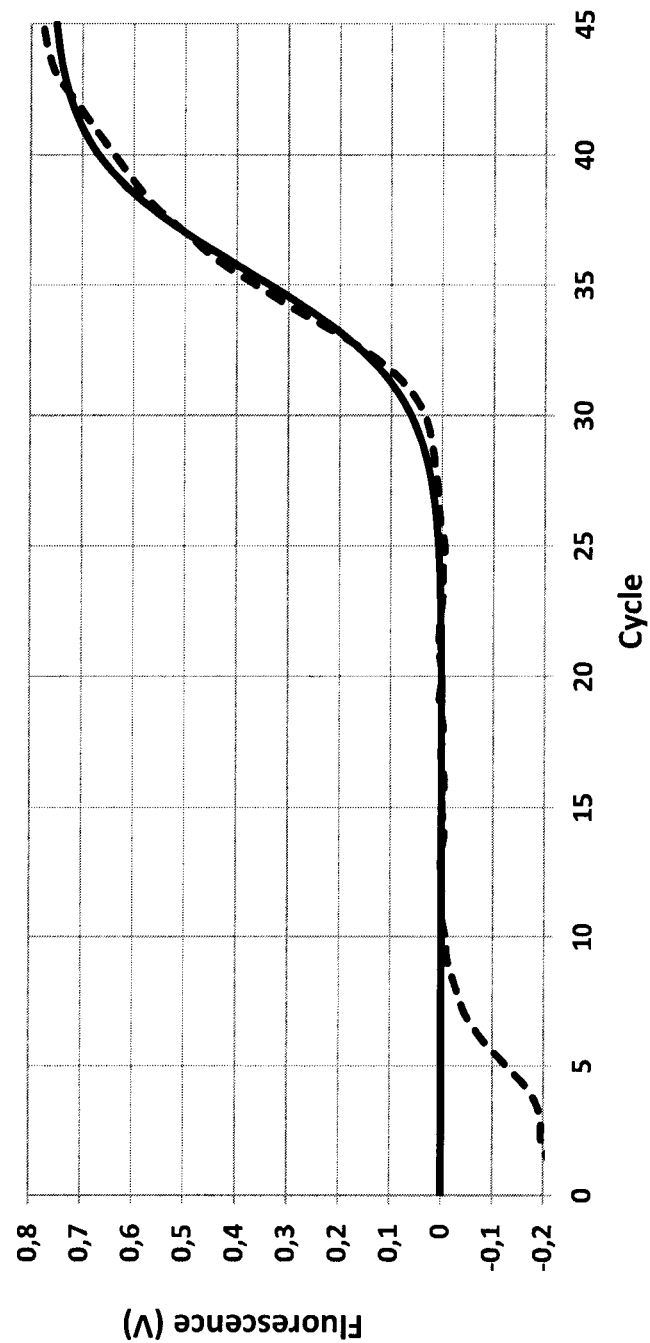
FIG. 17B shows example results for sigmoidal curve-fitting and FIG. 17C shows example results for the second derivative for sigmoidal curve-fitting.
Figure 17C:
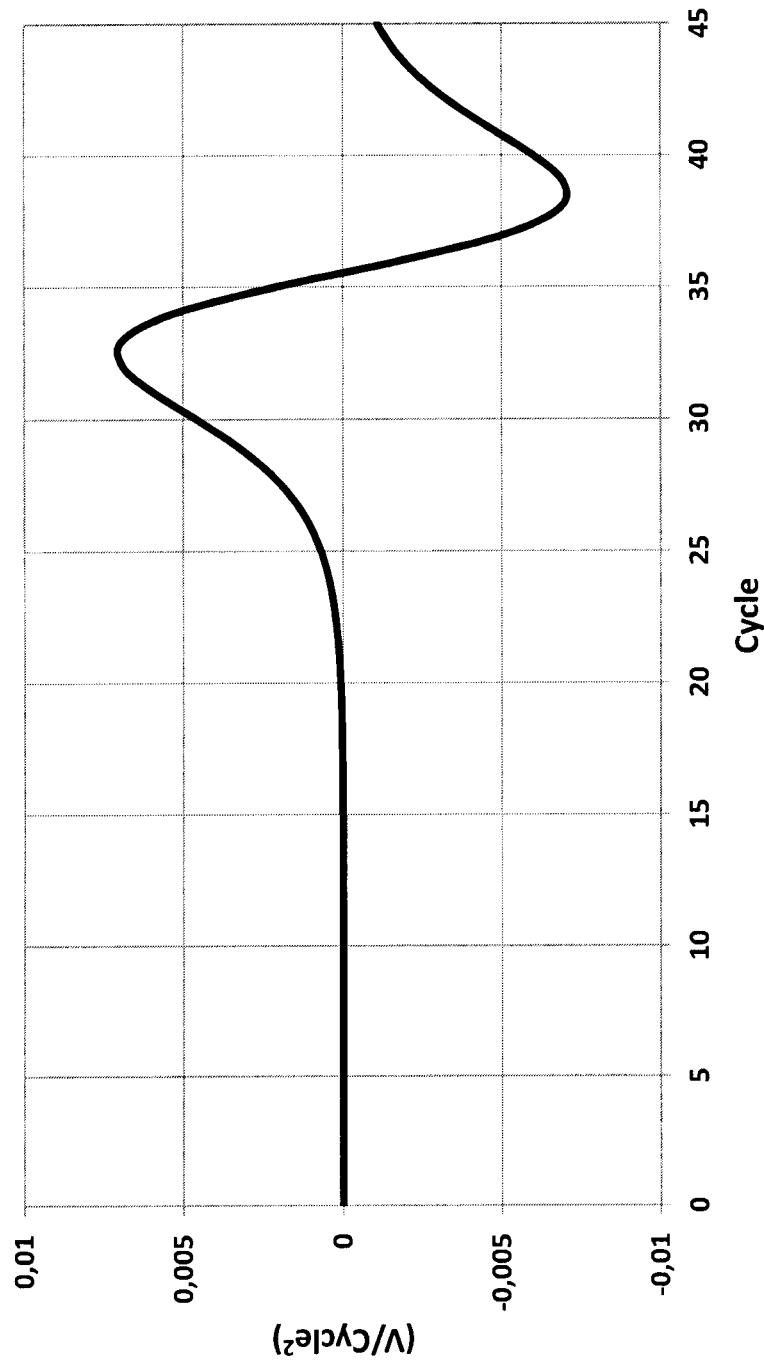

A least square best-fit algorithm was used to determine parameters a, b and $C_0$ in order that the SCF function difference with the background subtracted fluorescence readings is minimized. Correlation factors for each curve were also computed and $R^2$ values greater than 0.99 were generally observed for cycles 10 to 45. FIG. 17B shows typical results for sigmoidal curve-fitting (solid) vs. background subtracted fluorescence readings (dashed). The correlation coefficient $R^2$ is 0.9986 for cycles 10 to 45. FIG. 17C shows second derivative for the same data set. The cycle threshold is 32.54.

Figure 18A:
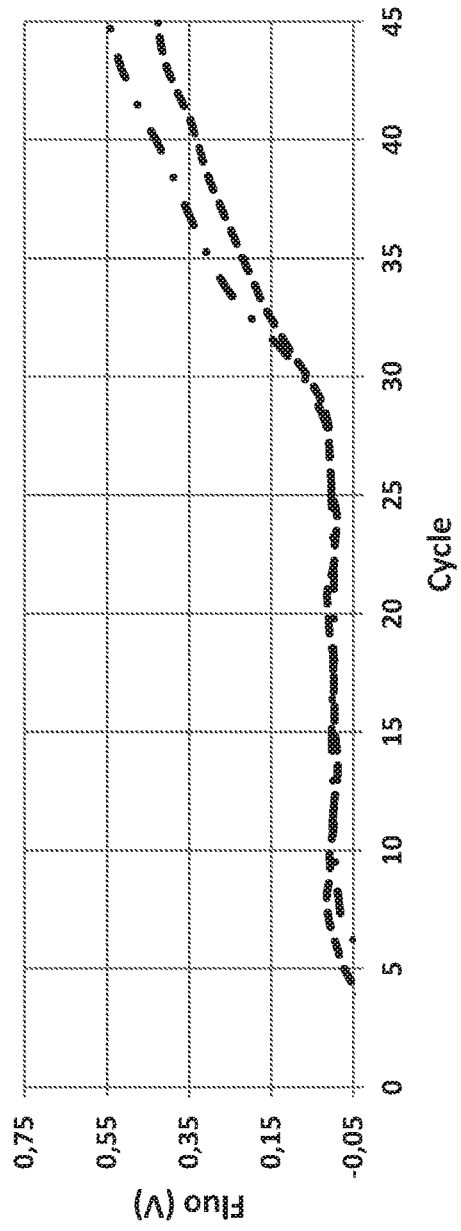
FIGS. 18A and 18B show the Raw data (bkg sub) and fitted curves for well 1 in an example experiment.
Figure 18B:
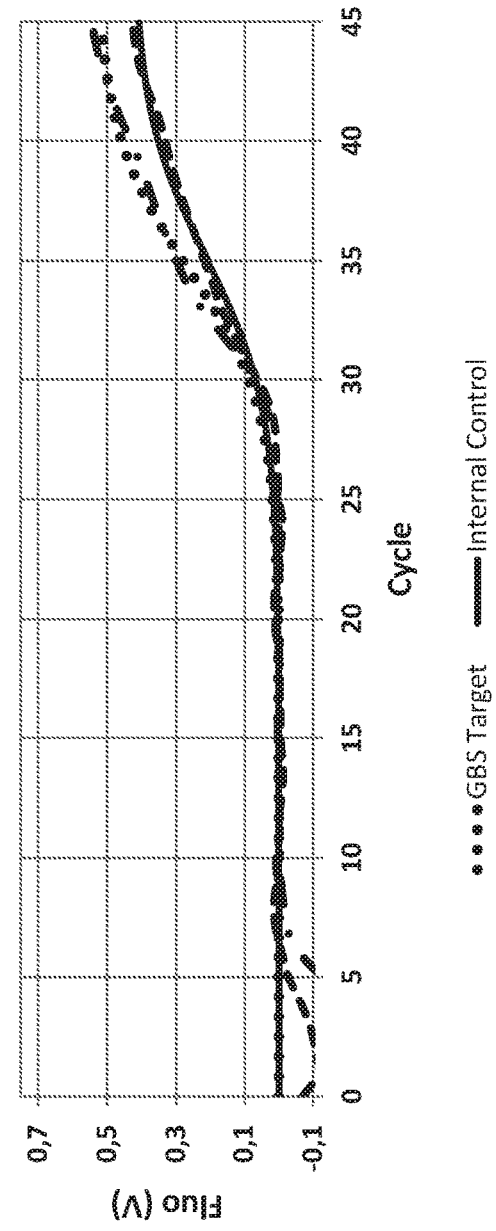
Figure 20A:
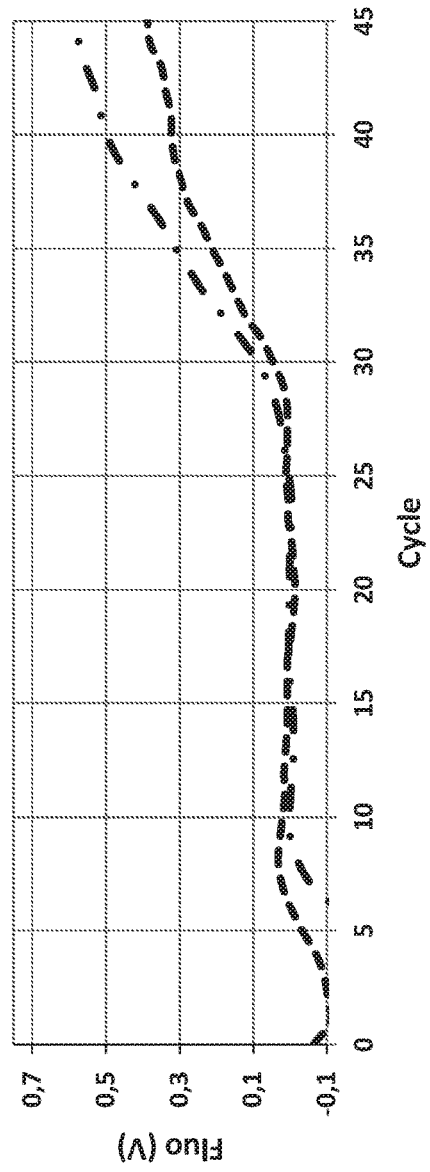
FIGS. 20A and 20B show the Raw data (bkg sub) and fitted curves for well 3 in the example experiment of FIG. 18.
Figure 20B:
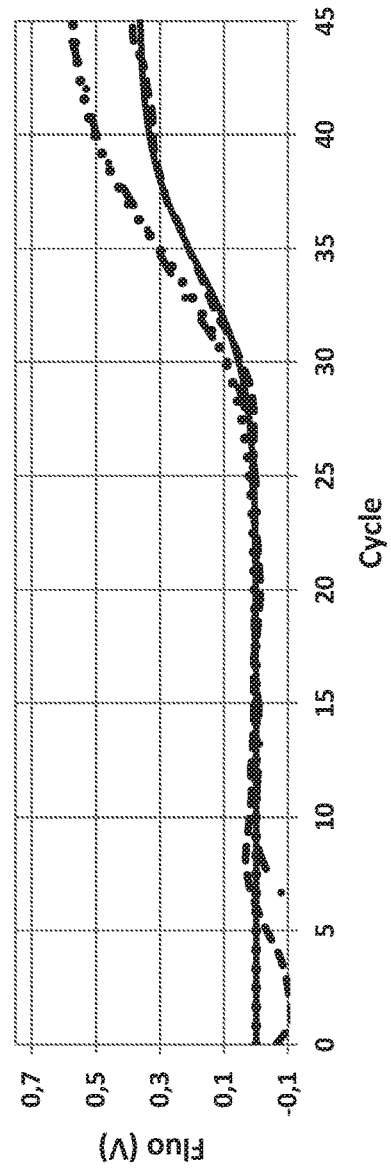

The results obtained are presented in FIGS. 18, 19 and 20. The positive control probes are labelled with FAM fluorophores. The fluorescence signal is represented by a blue trace (top curve(s) in each graph. Each well also contained an internal control that was amplified altogether with the target. The internal control probes are labelled with Cal-FluorRed610 fluorophores. The fluorescence signal is represented by a green trace (bottom curve(s) in each graph). FIGS. 18A, and 18B show the Raw data (bkg sub) and fitted curves for well 1. FIGS. 19A and 19B show the Raw data (bkg sub) and fitted curves for well 2 and FIGS. 20A and 20B show the Raw data (bkg sub) and fitted curves for well 3.

The PCR data shows that it is possible to use the Optical Interrogation Device to measure, in real time, the fluorescence generated by two different fluorophores (different excitation/emission wavelengths) during a PCR amplification run into 3 adjacent wells on the same microfluidic device.

As will be readily understood, numerous modifications could be made to the embodiments above without departing from the scope of the invention.

The embodiments described above are intended to be exemplary only. The scope of the invention is therefore intended to be limited solely by the appended claims.

The invention claimed is:

1. An interrogation device for detecting luminescent light produced by analytes in a sample excited by multiple excitation light beams each having individual spectral contents, comprising:
a plurality of light sources each generating one of said multiple excitation light beams, the excitation light beams being projected on a common excitation site on the sample to excite the analytes;
at least one detector for detecting the luminescent light produced by the sample; and
an optical assembly having:
common sample-side optics projecting the excitation light beams towards said sample and collecting luminescent light from said sample;
a main axis from said common sample-side optics to said at least one detector, said plurality of light sources being peripherally distributed about said main axis;
distinct and fixed excitation light paths for each of the excitation light beams from said peripherally distributed light sources to said common excitation site on said sample;
a shared luminescence light path for the luminescent light propagating rearward from the common excitation site on sample to the at least one detector;
an inwardly-redirecting assembly provided in said excitation light paths for inwardly redirecting said excitation light beams into said common sample-side optics close to said main axis and toward the common excitation site; and
wherein said excitation light paths and said shared luminescence light path are on a same side of said sample and said common sample-side optics is present in all of said excitation light paths and in said shared luminescence light path, and wherein said inwardly-redirecting assembly comprises an outer reflective element and an inner reflective element cooperating to receive the excitation light beams and redirect said excitation light beams toward said common sample-side optics.

2. The interrogation device as claimed in claim 1, wherein said optical assembly further comprises a filter provided in said shared luminescence light path, wherein said filter is one of a fixed filter and an actuated filter and wherein said filter is one of a single-band-pass filter and a multi-band-pass filter.

3. The interrogation device as claimed in claim 1, wherein the optical assembly is contained in a single housing.

4. The interrogation device as claimed in claim 1, wherein the optical assembly includes a component to shape at least one of a spatial and a spectral profile of at least one of said excitation light beam and said luminescent light.

5. The interrogation device as claimed in claim 4, wherein said component is a spatial filter limiting a size of a given light beam along a corresponding light path.

6. The interrogation device as claimed in claim 5, wherein said optical assembly includes a spectral filter and wherein said spectral filter has a spectral profile excluding the spectral contents of the excitation beam and is disposed in the shared luminescence light path.

7. The interrogation device as claimed in claim 1, wherein the optical assembly includes detector-side optics outputting the filtered luminescent light for detection.

8. The interrogation device as claimed in claim 1, wherein said optical assembly comprises waveguides to guide said excitation light beams towards said sample-side optics.

9. The optical interrogation device as claimed in claim 1, wherein said luminescent light produced from analytes in said sample results from at least one optical phenomena, said optical phenomena being one of fluorescence, phosphorescence, bioluminescence, time-resolved luminescence and polarization fluorescence.

10. A test apparatus for optically testing a sample, including:
an optical interrogation device as claimed in claim 1.

11. The test apparatus as claimed in claim 10, wherein said test apparatus is embodied by a system for performing one of Polymerase Chain Reaction (PCR), real-time Polymerase Chain Reaction (rtPCR), isothermal amplification Recombination Polymerase Amplification (RPA) and other nucleic acid detection methods.

* * * * *